(12) United States Patent
Dogué et al.

(10) Patent No.: US 12,648,782 B2
(45) Date of Patent: *Jun. 9, 2026

(54) THREADED TARGETING INSTRUMENTS, SYSTEMS AND METHODS OF USE

(71) Applicant: Paragon 28, Inc., Englewood, CO (US)

(72) Inventors: Joseph Dogué, Aurora, CO (US); Albert Dacosta, Lone Tree, CO (US); Francis D. Barmes, Parker, CO (US); Spanky Raymond, Uniontown, OH (US); Laura Zagrocki Brinker, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/823,478

(22) Filed: Sep. 3, 2024

(65) Prior Publication Data

US 2024/0423651 A1     Dec. 26, 2024

Related U.S. Application Data

(63) Continuation of application No. 17/445,112, filed on Aug. 16, 2021, now Pat. No. 12,076,031, which is a continuation of application No. PCT/US2020/018129, filed on Feb. 13, 2020.

(60) Provisional application No. 62/805,777, filed on Feb. 14, 2019.

(51) Int. Cl.
*A61B 17/17*      (2006.01)
*A61B 17/56*      (2006.01)

(52) U.S. Cl.
CPC ...... *A61B 17/1775* (2016.11); *A61B 17/1717* (2013.01); *A61B 2017/565* (2013.01)

(58) Field of Classification Search
CPC . A61B 17/1775; A61B 17/1717; A61B 17/56; A61B 17/8897; A61B 2017/565
USPC .......................................................... 606/96
See application file for complete search history.

(56) References Cited

U.S. PATENT DOCUMENTS

| | | | |
|---|---|---|---|
| 2007/0055286 A1* | 3/2007 | Ralph | A61B 17/1728 606/96 |
| 2013/0012953 A1* | 1/2013 | Chan | A61B 17/1682 606/148 |
| 2013/0190765 A1* | 7/2013 | Harris | A61F 2/46 606/87 |
| 2015/0359580 A1* | 12/2015 | Dacosta | A61B 17/17 606/281 |
| 2018/0242988 A1* | 8/2018 | Dacosta | A61B 17/1775 |

* cited by examiner

*Primary Examiner* — Jessica Weiss
(74) *Attorney, Agent, or Firm* — Heslin Rothenberg Farley & Mesiti P.C.; Jacquelyn A. Graff, Esq.

(57) ABSTRACT

Instruments, implants, bone plates, systems and methods for correcting bone deformities and fractures in the lower extremity are disclosed. Specifically, targeting instruments, implants, bone plates, systems and methods used for correcting bone deformities and/or fractures in the foot using compression are disclosed.

17 Claims, 34 Drawing Sheets

100

100

100

110

110

110

110

110

110

110

160

160

160

160

160

180

180

180

180

180

THREADED TARGETING INSTRUMENTS, SYSTEMS AND METHODS OF USE

CROSS REFERENCE TO RELATED APPLICATION

This application is a continuation of U.S. application Ser. No. 17/445,112 filed Aug. 16, 2021 and which will issue on Sep. 3, 2024 as U.S. Pat. No. 12,076,031, which is a continuation of PCT/US2020/018129 filed Feb. 13, 2020 and entitled Threaded Targeting Instruments, Systems and Methods of Use, which claims priority benefit under 35 U.S.C. § 119(e) of U.S. Provisional Application No. 62/805, 777 filed Feb. 14, 2019 and entitled Threaded Targeting Instruments, Systems and Methods of Use, which are incorporated herein by reference in their entireties.

FIELD OF THE INVENTION

The present invention relates generally to general surgery, podiatric, and orthopaedic instruments used for correcting bone deformities. More specifically, but not exclusively, the present invention relates to instruments, implants, plates, systems and methods for correcting bone deformities.

BACKGROUND OF THE INVENTION

Many currently available instruments used in conjunction with implants for correcting bone deformities and fractures use various alignment mechanisms. The currently available instruments may experience problems with adequate surgical exposure, alignment variability, inaccurate targeting and instability. Thus, new instruments and methods of use are needed to ensure proper and reproducible orientation of corrective or stabilization devices to be implanted into the foot and ankle.

SUMMARY OF THE INVENTION

Aspects of the present invention provide instruments, implants, plates, systems and methods for correcting bone deformities in the foot.

In one aspect, provided herein is a targeting guide. The targeting guide includes a guide arm, a guide tube coupled to the guide arm, and a guide pin that is movably engaged to an end of the guide arm.

In another aspect, provided herein is a method of using the targeting guide to secure two bones together. The method includes, inserting a guide pin into a bone and securing an implant holder to a bone plate. The method also includes securing a guide arm to the guide pin at a second end of the guide arm and securing an intermediate portion of the guide arm within a channel of the implant holder. In addition, the method includes inserting a guide tube into a first end of the guide arm and inserting a drill guide into a through hole of the guide tube. Next, the method includes inserting a protector member into a through hole of the drill guide and inserting a target pin through the protector member and into at least one bone. The method also includes inserting two anchoring wires through two protrusions positioned on a housing element at the second end of the guide arm and removing guide pin from the guide arm. The method further includes inserting the target pin entirely through a first metatarsal extending proximally into a talus and removing the protector member from the drill guide. The method also includes rotating the guide tube to perform joint reduction and drilling a hole over the target pin. Further, the method includes threading an implant through the drill guide and into the bones to secure at least two bones.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein are instruments, implants, plates, and systems for correcting bone deformities. Further, methods for correcting bone deformities using instruments, implants, plates, and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current instrumentation and methods are described herein with reference to use with the bones of the foot, the bones of the foot, ankle and lower leg may be used to describe the surfaces, positions, directions or orientations of the instrumentation and methods. Further, the instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the instrumentation and methods, and the aspects, components, features and the like thereof, described herein with respect to the right foot may be mirrored so that they likewise function with the left foot. Further, the instrumentation and methods, and the aspects, components, features and the like thereof, disclosed herein are described with respect to the foot for brevity purposes, but it should be understood that the instrumentation and methods may be used with other bones of the body having similar structures.

Figure 1:
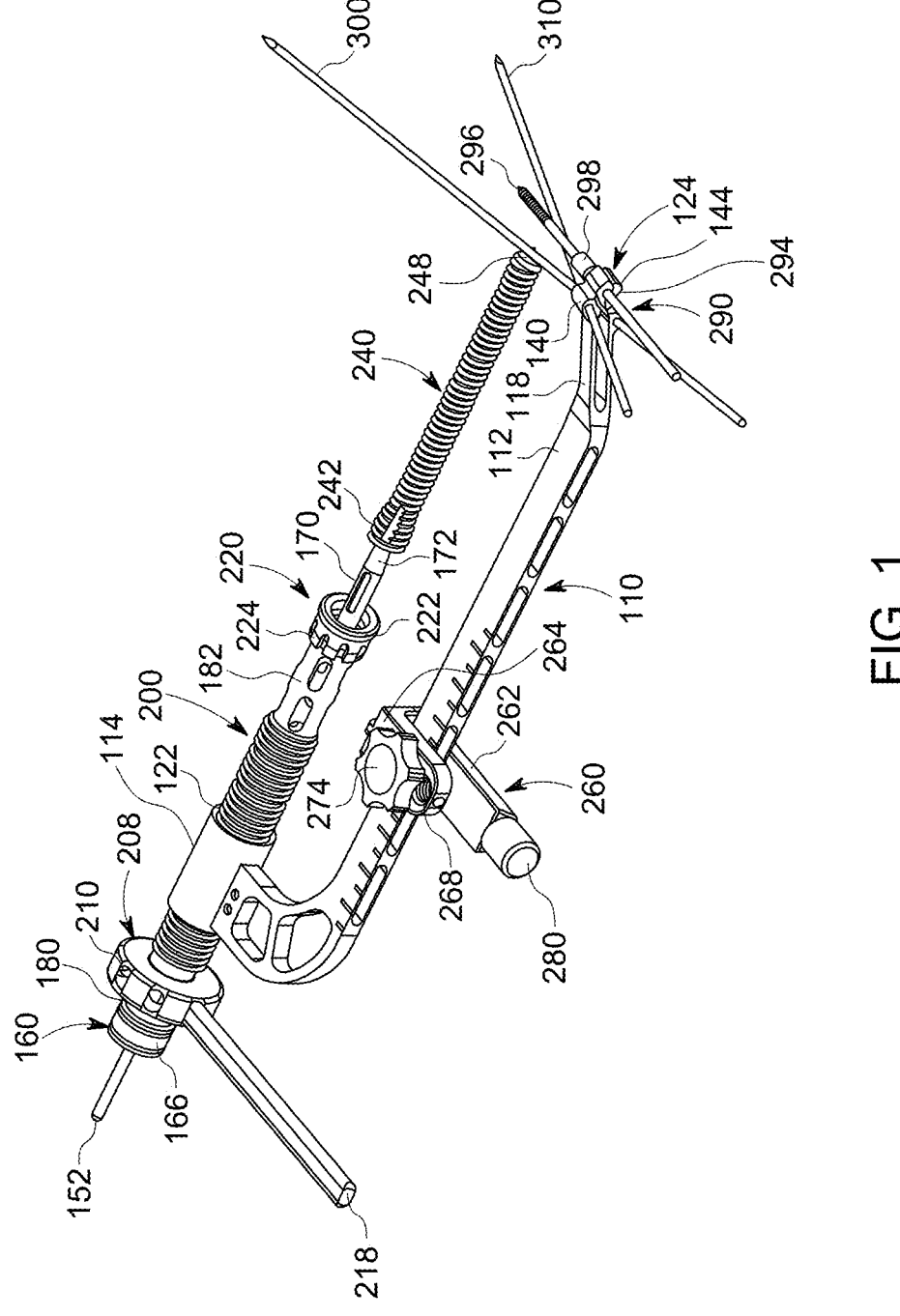
FIG. 1 is a first side perspective view of one embodiment of a targeting guide, in accordance with an aspect of the present invention.
Figure 2:
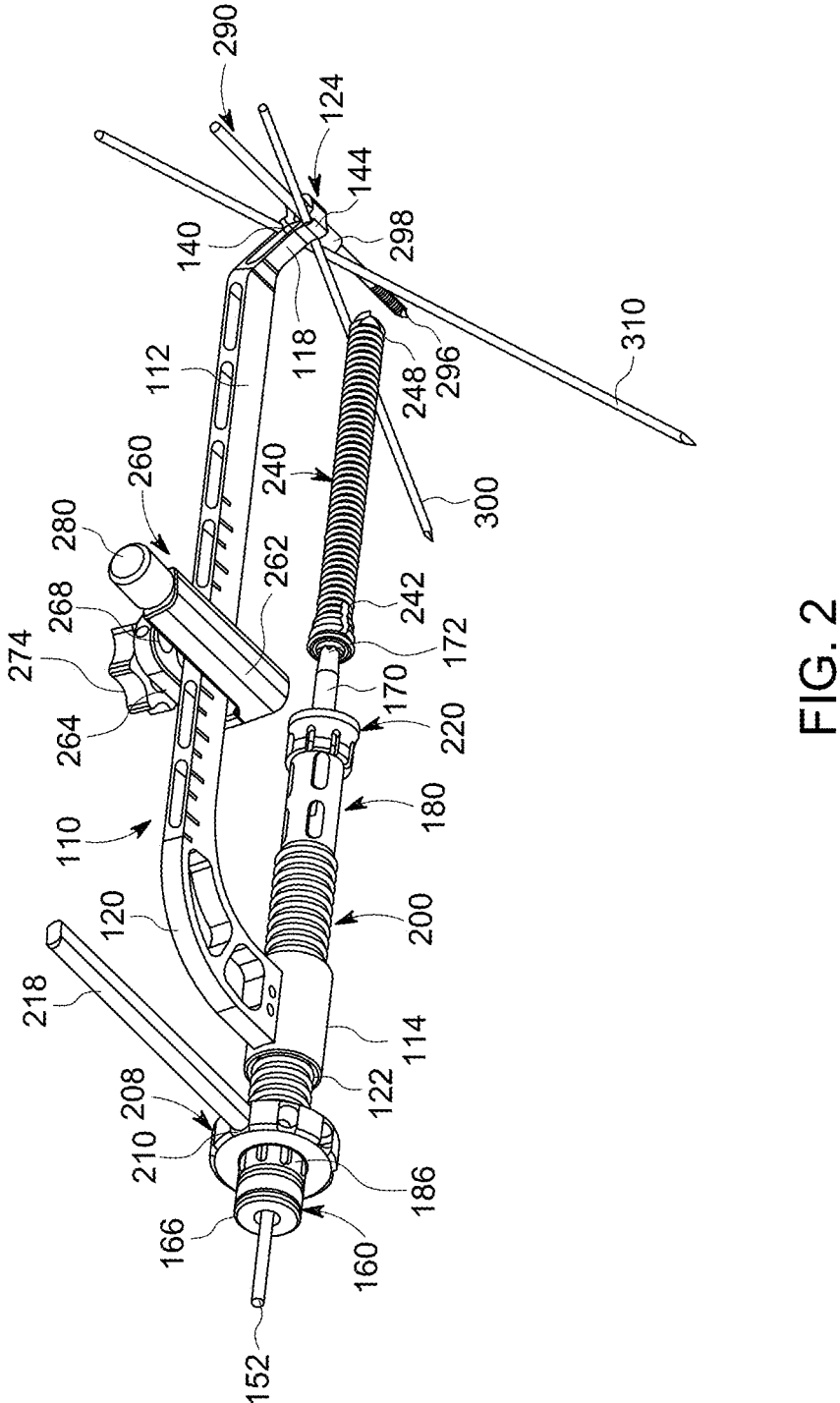
FIG. 2 is a second side perspective view of the targeting guide of FIG. 1, in accordance with an aspect of the present invention.
Figure 3:
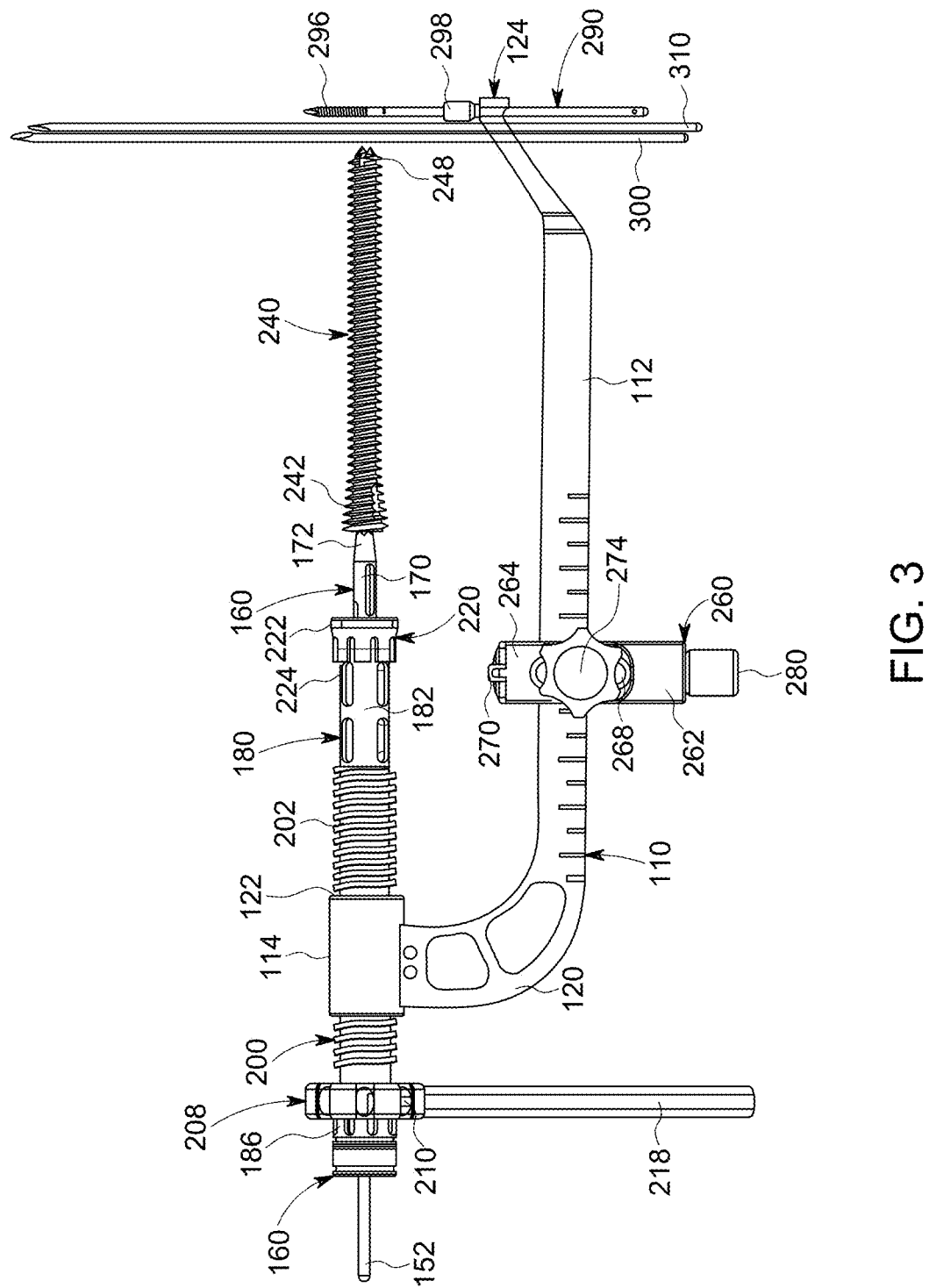
FIG. 3 is a bottom view of the targeting guide of FIG. 1, in accordance with an aspect of the present invention.
Figure 4:
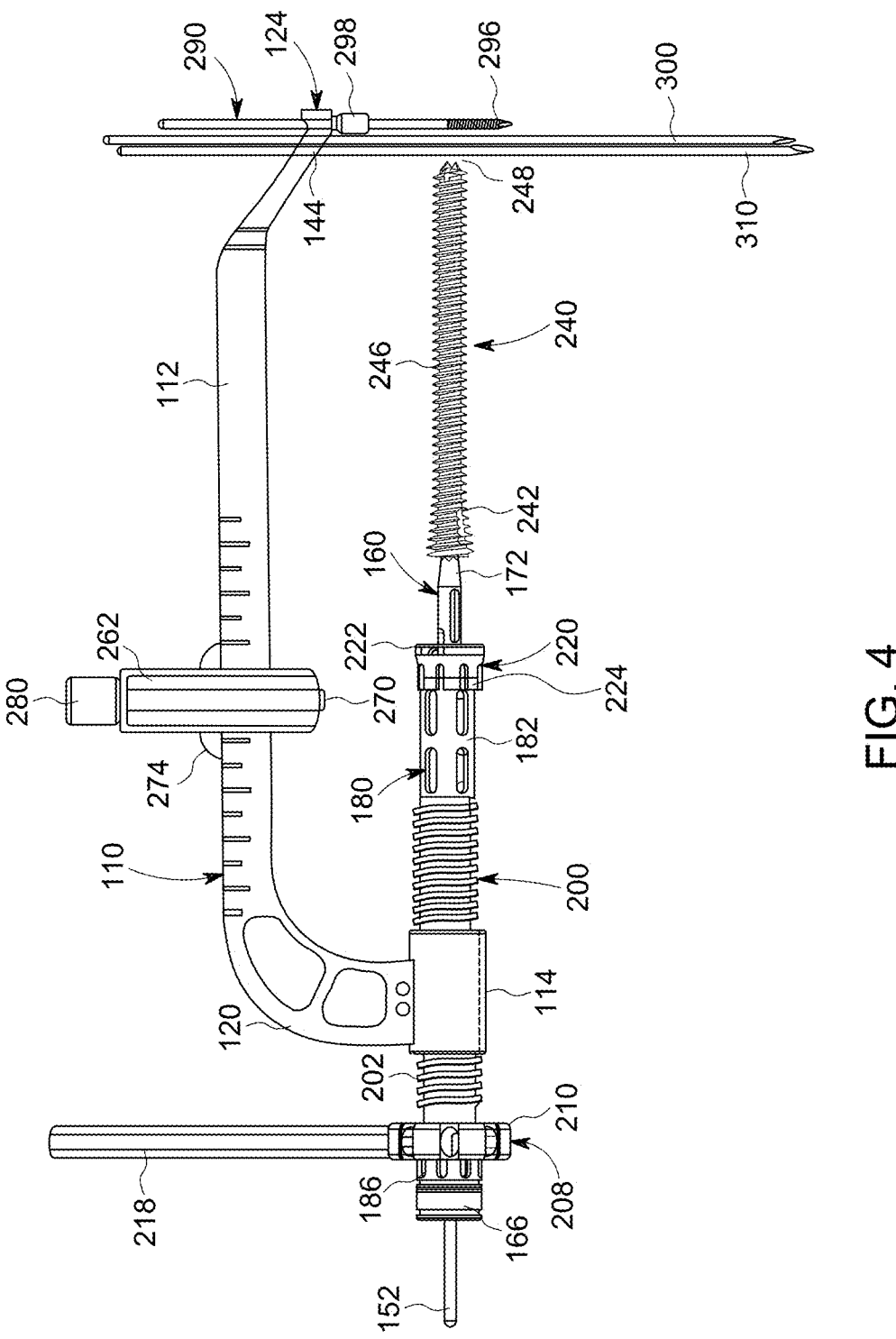
FIG. 4 is a top view of the targeting guide of FIG. 1, in accordance with an aspect of the present invention.
Figure 5:
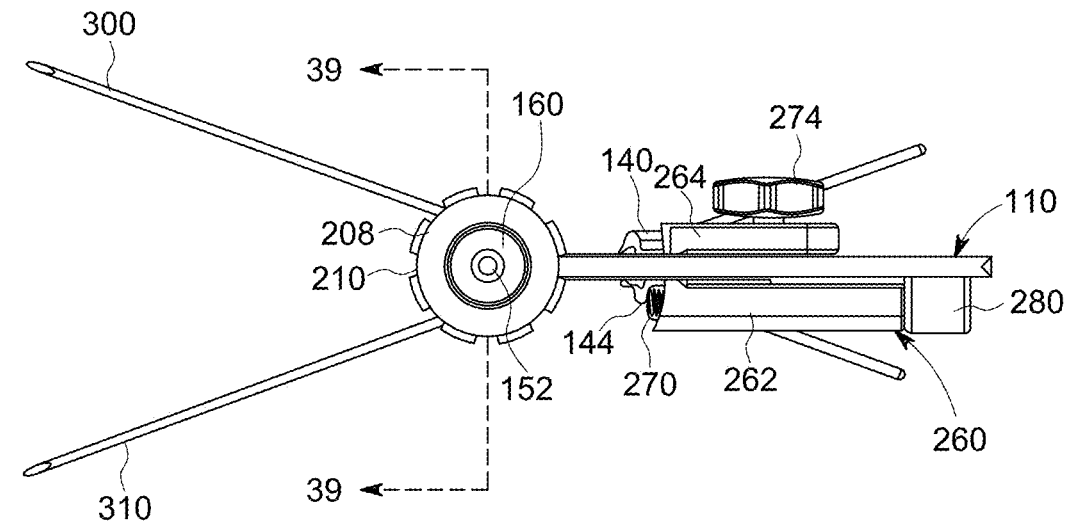
FIG. 5 is a first end view of the targeting guide of FIG. 1, in accordance with an aspect of the present invention.
Figure 6:
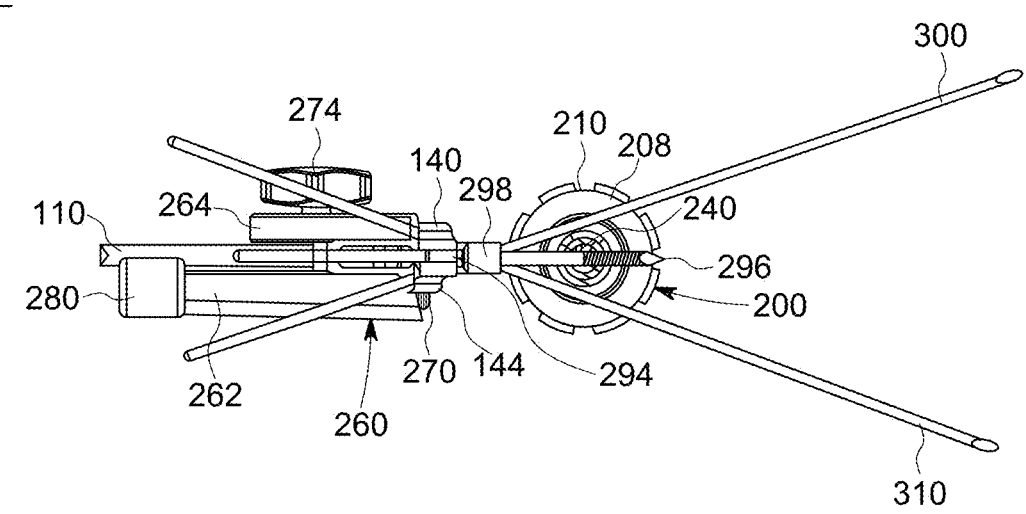
FIG. 6 is a second end view of the targeting guide of FIG. 1, in accordance with an aspect of the present invention.
Figure 7:
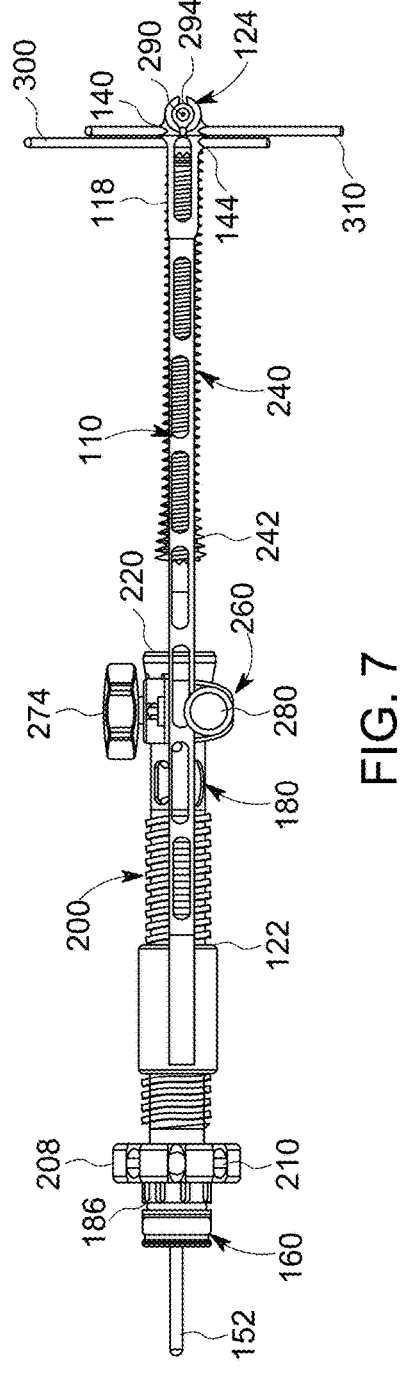
FIG. 7 is a first side view of the targeting guide of FIG. 1, in accordance with an aspect of the present invention.
Figure 8:
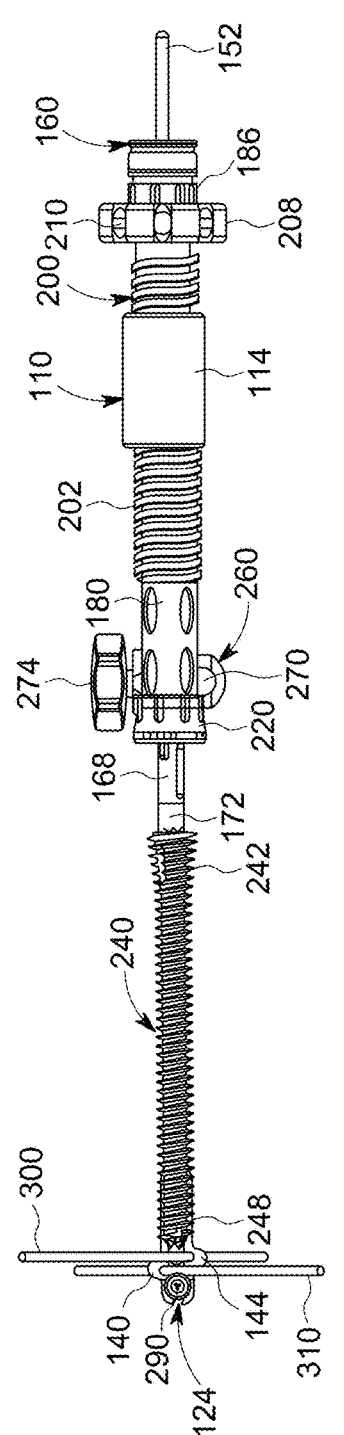
FIG. 8 is a second side view of the targeting guide of FIG. 1, in accordance with an aspect of the present invention.
Figure 9:
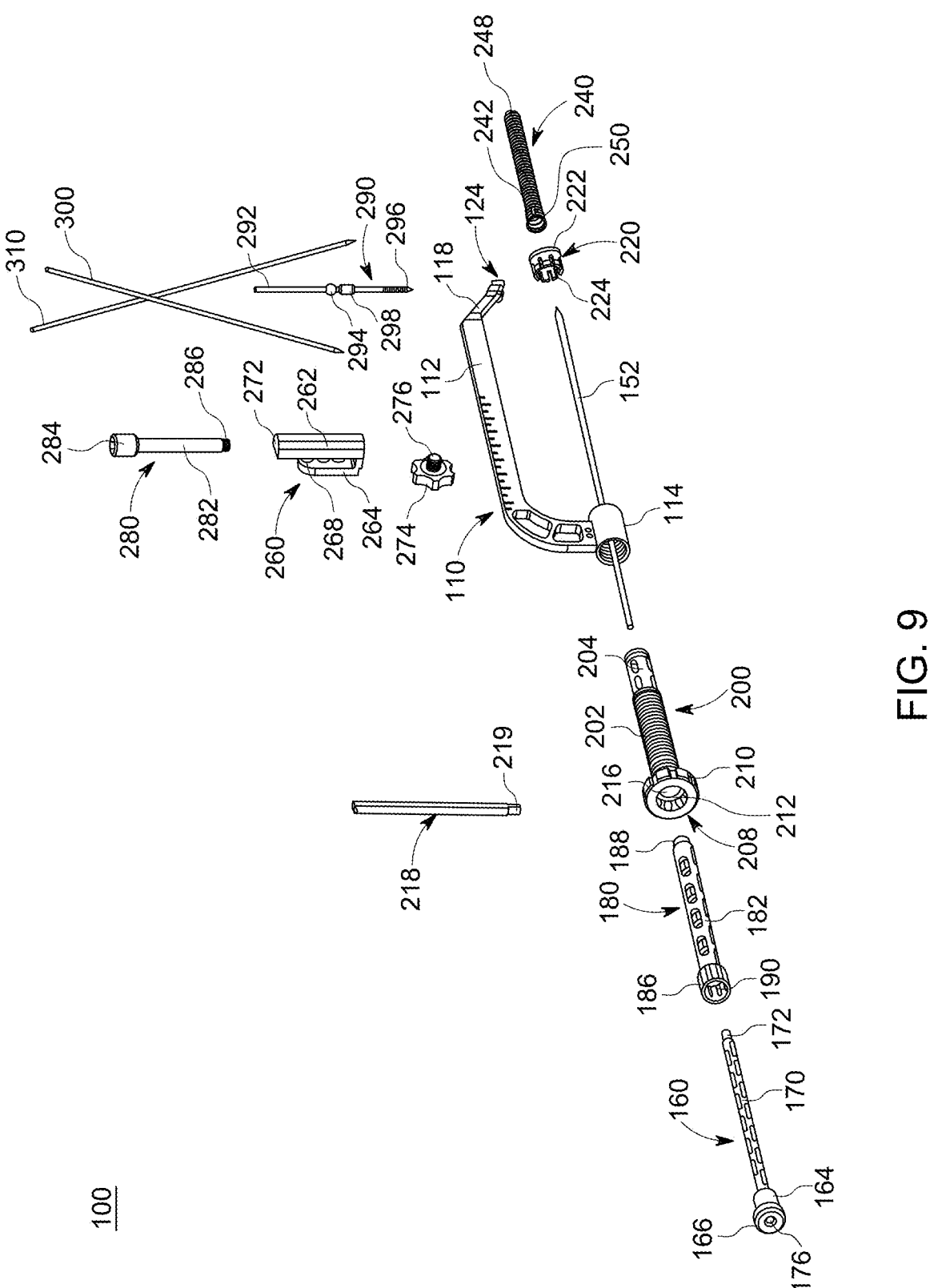
FIG. 9 is an exploded, first perspective view of the targeting guide of FIG. 1, in accordance with an aspect of the present invention.
Figure 10:
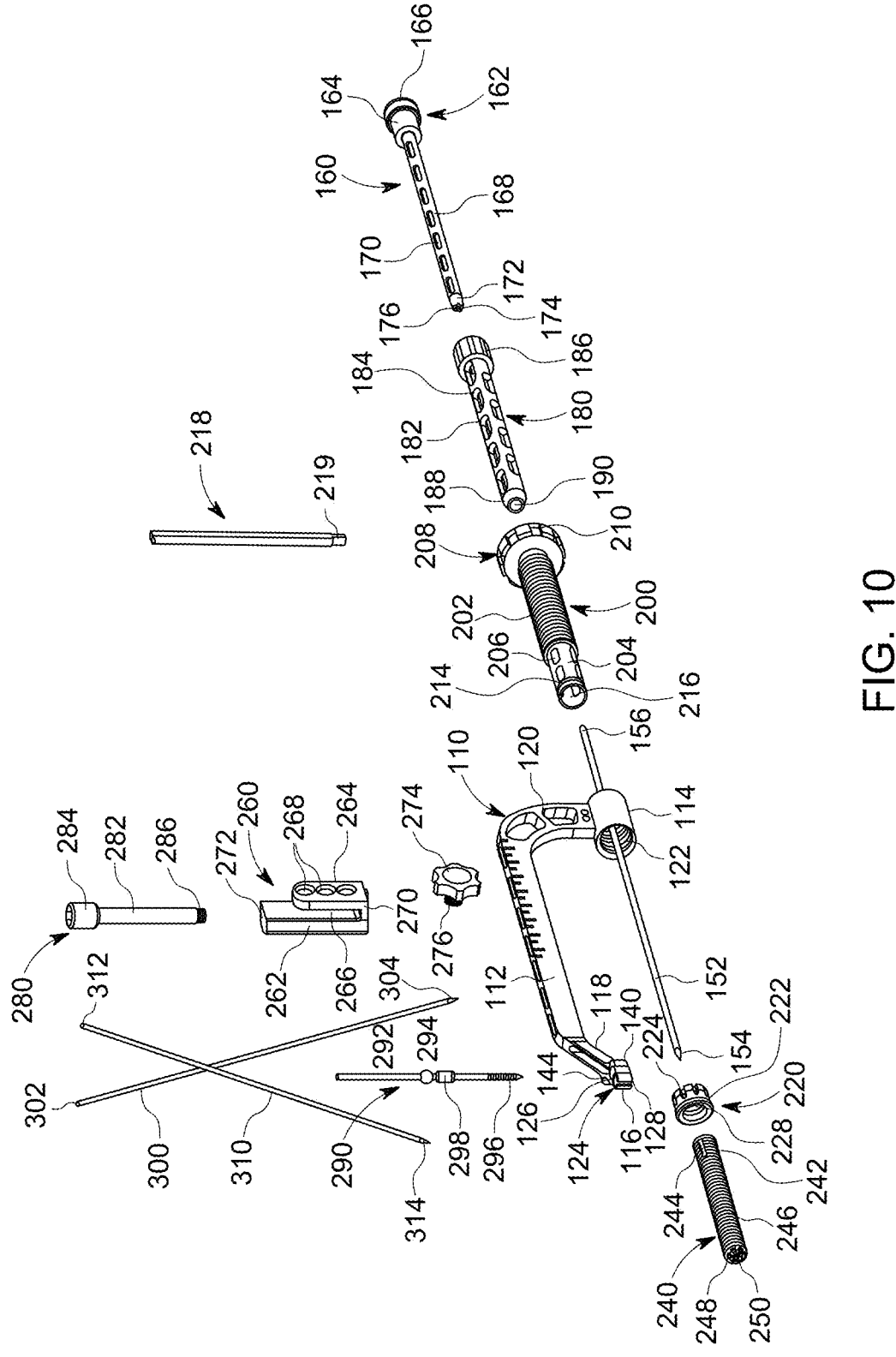
FIG. 10 is an exploded, second perspective view of the targeting guide of FIG. 1, in accordance with an aspect of the present invention.
Figure 11:
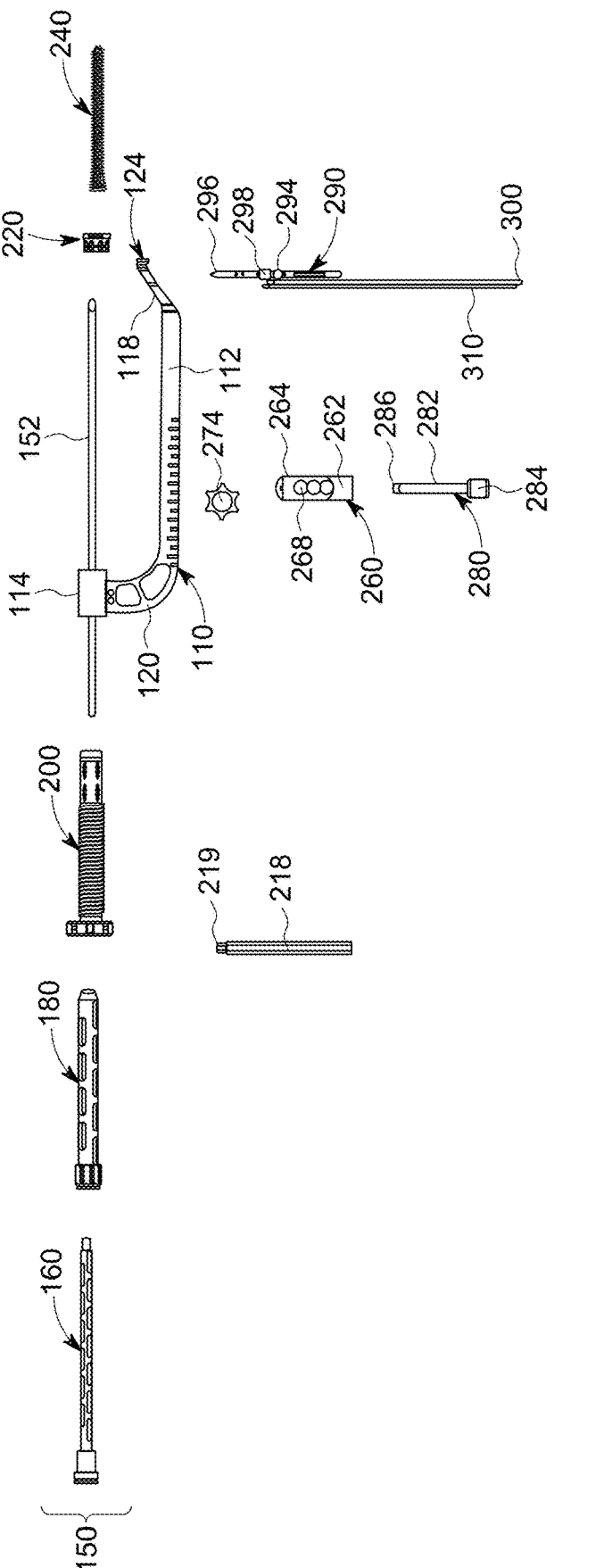
FIG. 11 is an exploded, bottom view of the targeting guide of FIG. 1, in accordance with an aspect of the present invention.
Figure 12:
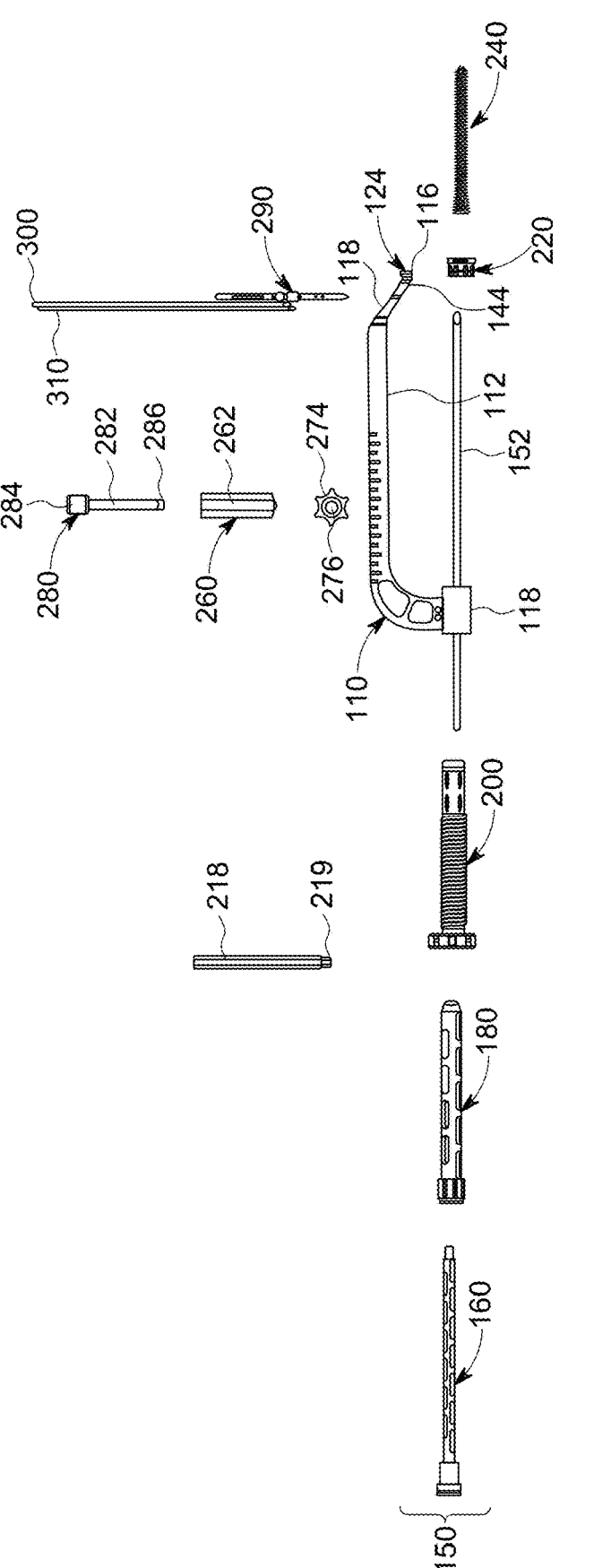
FIG. 12 is an exploded, top view of the targeting guide of FIG. 1, in accordance with an aspect of the present invention.
Figure 13:
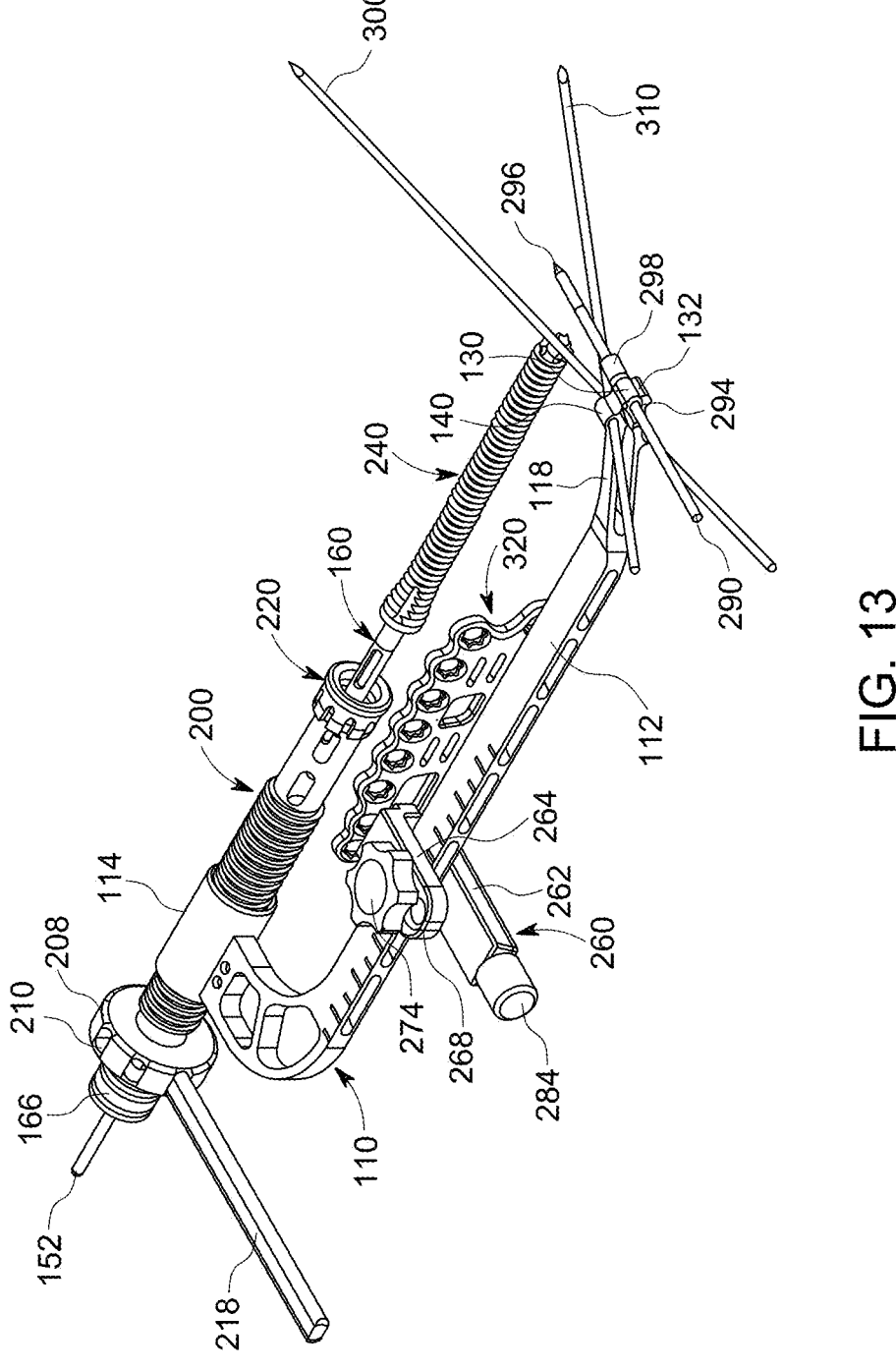
FIG. 13 is a first perspective view of the targeting guide of FIG. 1 with a coupled bone plate, in accordance with an aspect of the present invention.
Figure 14:
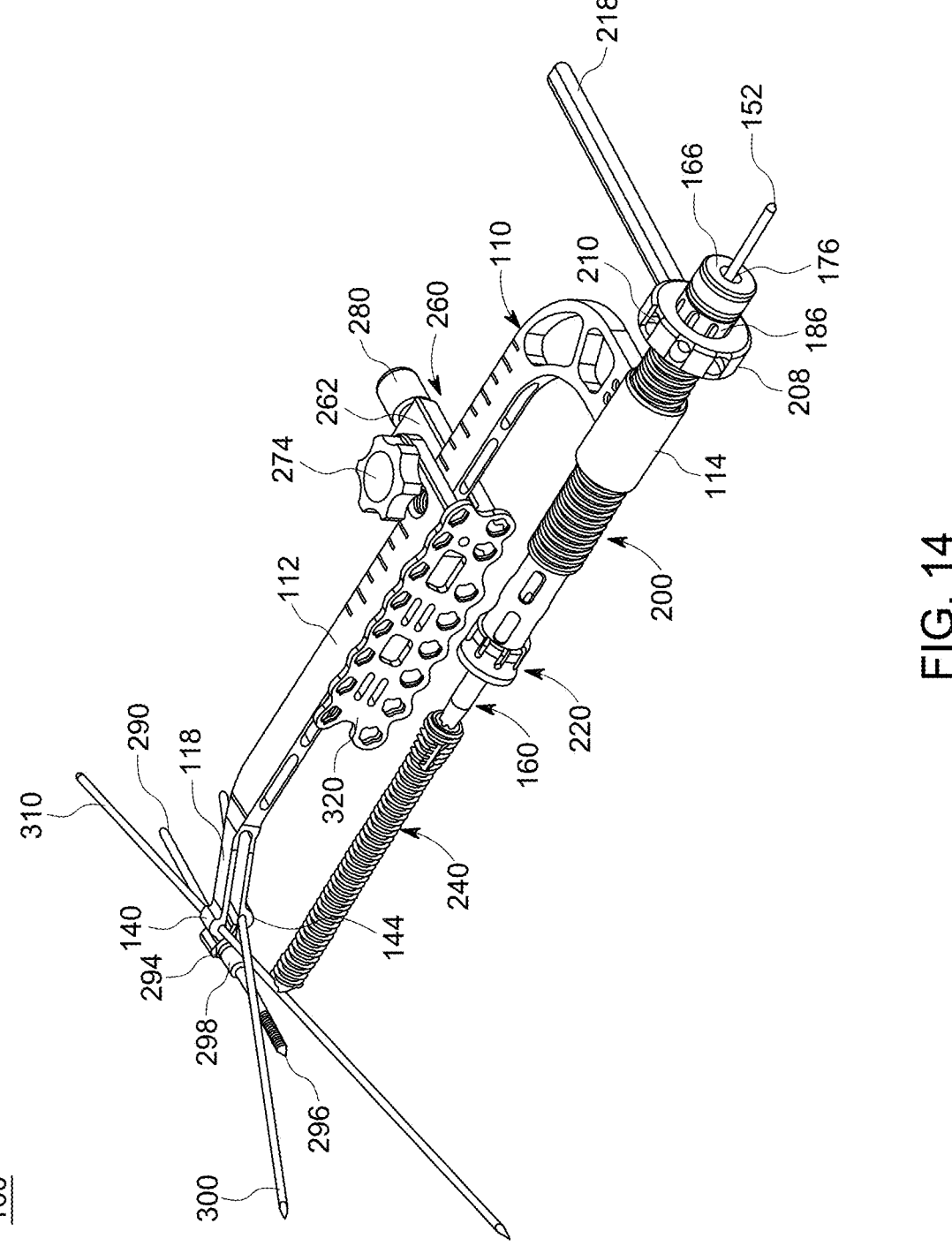
FIG. 14 is a second perspective view of the targeting guide and the bone plate of FIG. 13, in accordance with an aspect of the present invention.
Figures 15, 16:
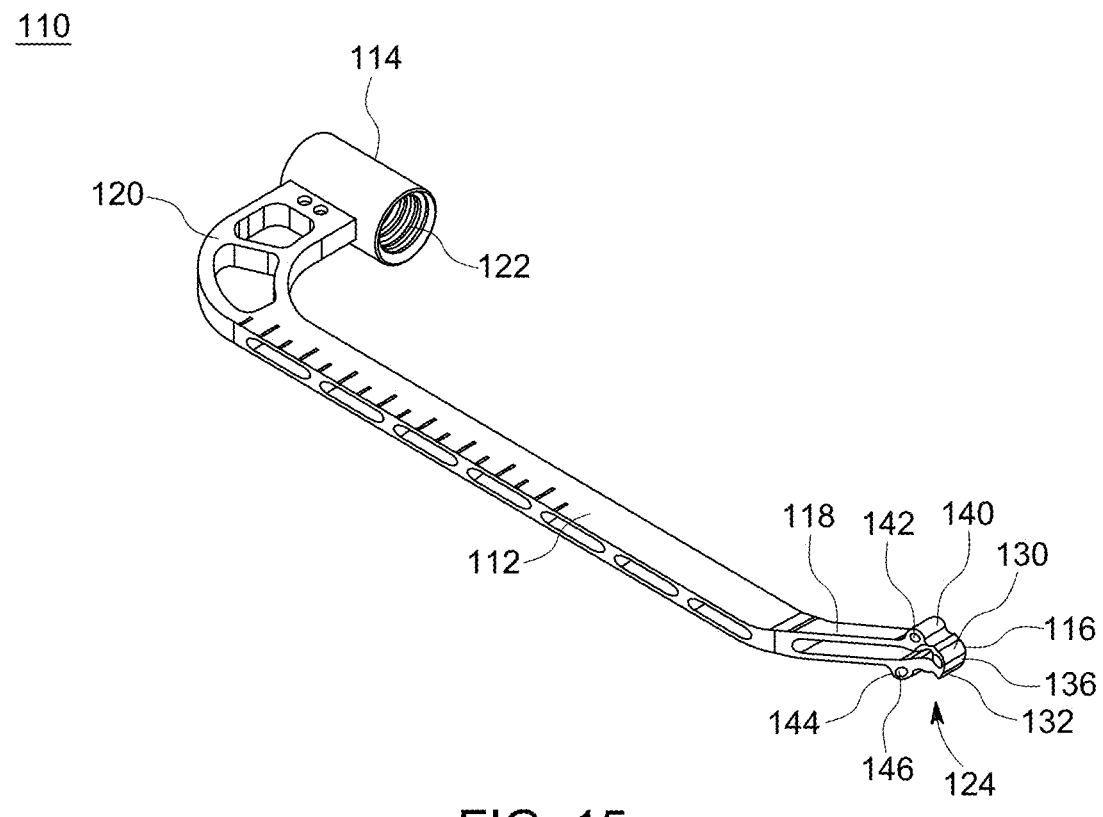
FIG. 15 is a first perspective view of the guide arm of the targeting guide of FIG. 1, in accordance with an aspect of the present invention.
FIG. 16 is a second perspective view of the guide arm of FIG. 15, in accordance with an aspect of the present invention.
Figure 17:
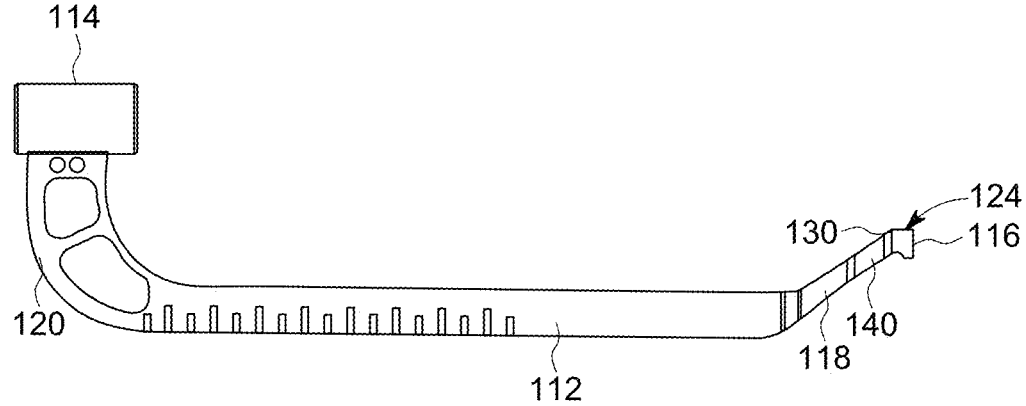
FIG. 17 is a bottom view of the guide arm of FIG. 15, in accordance with an aspect of the present invention.
Figure 18:
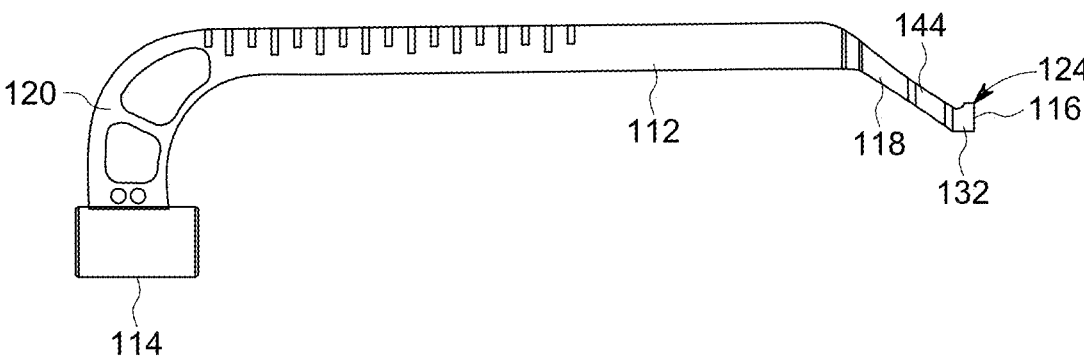
FIG. 18 is a top view of the guide arm of FIG. 15, in accordance with an aspect of the present invention.
Figure 19:
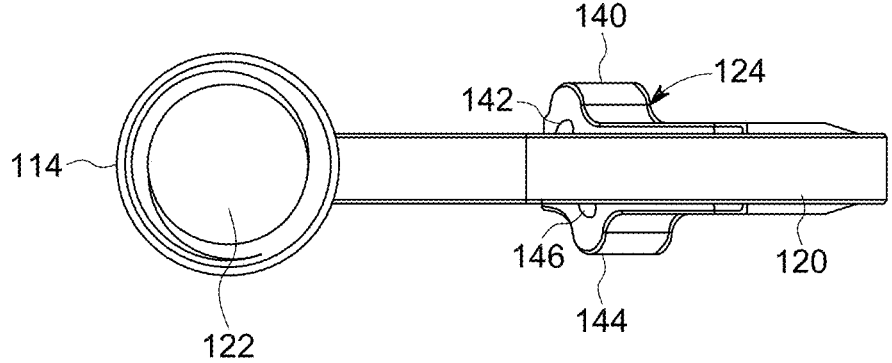
FIG. 19 is a first end view of the guide arm of FIG. 15, in accordance with an aspect of the present invention.
Figure 20:
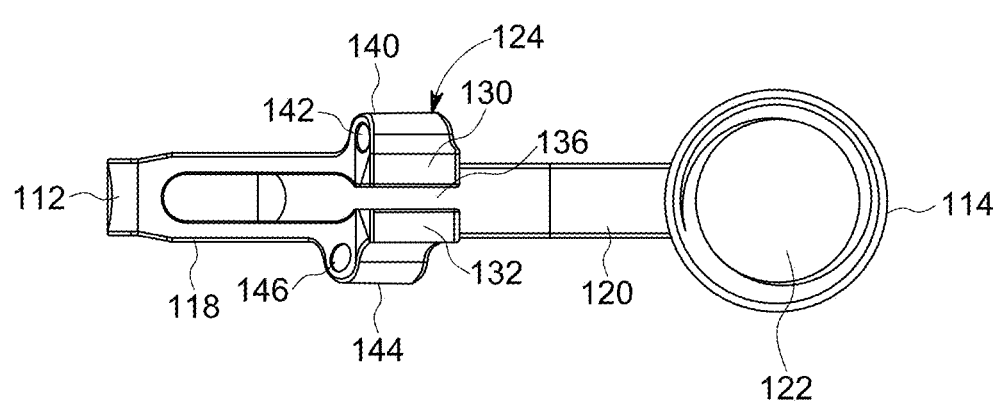
FIG. 20 is a second end view of the guide arm of FIG. 15, in accordance with an aspect of the present invention.
Figure 21:
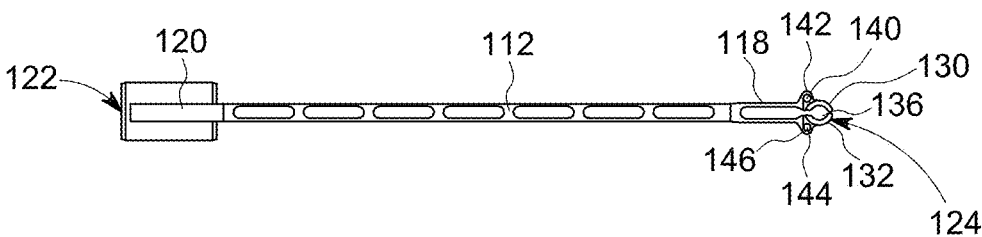
FIG. 21 is a first side view of the guide arm of FIG. 15, in accordance with an aspect of the present invention.
Figure 22:
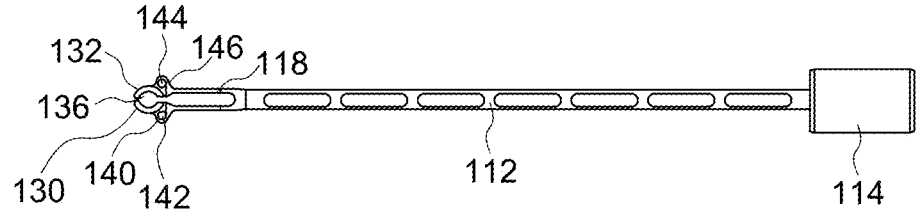
FIG. 22 is a second side view of the guide arm of FIG. 15, in accordance with an aspect of the present invention.
Figure 23:
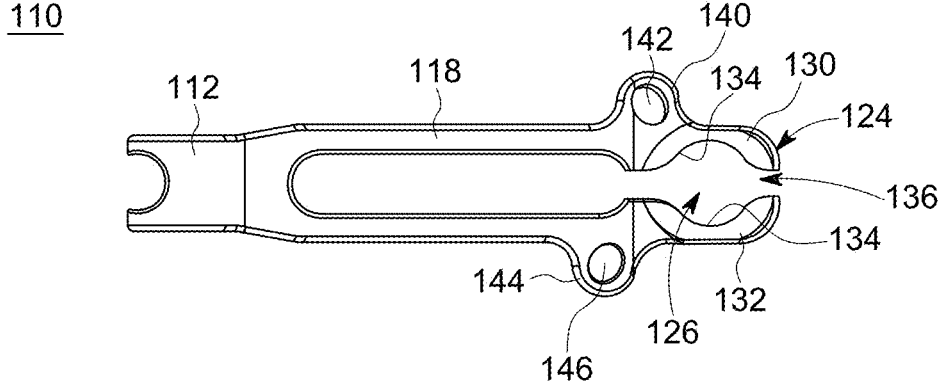
FIG. 23 is an enlarged view of the second end of the guide arm of FIG. 15, in accordance with an aspect of the present invention.
Figure 24:
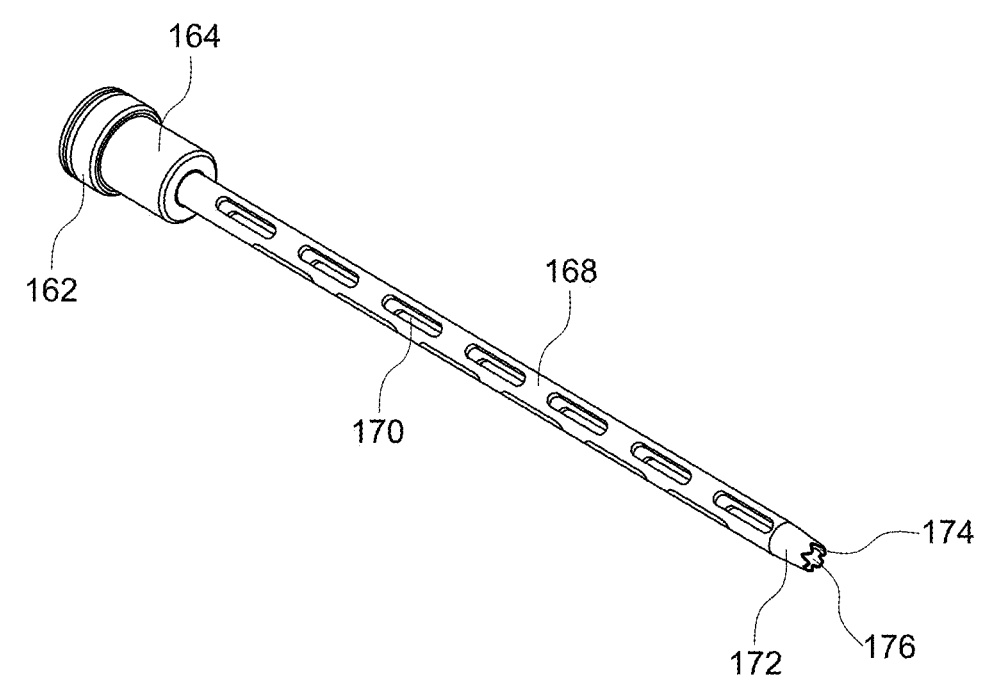
FIG. 24 is a first perspective view of the protector member of the targeting guide of FIG. 1, in accordance with an aspect of the present invention.
Figure 25:
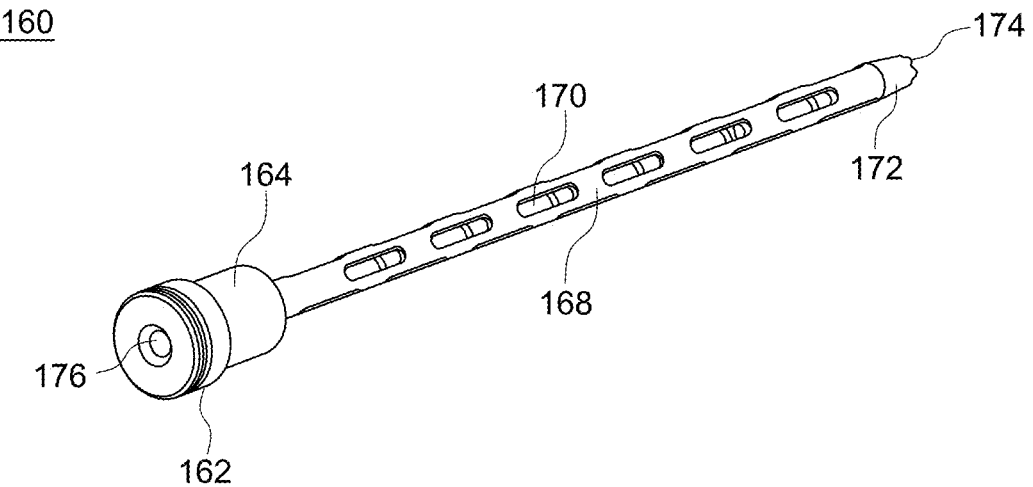
FIG. 25 is a second perspective view of the protector member of FIG. 24, in accordance with an aspect of the present invention.
Figure 26:
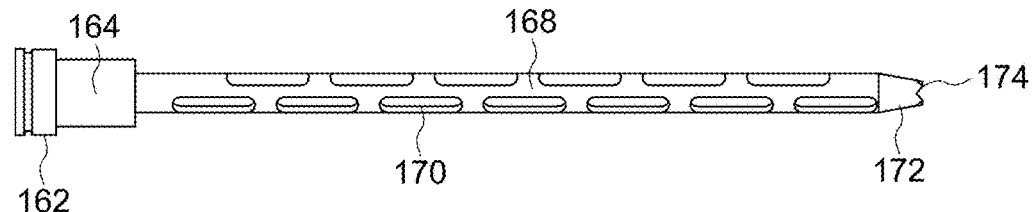
FIG. 26 is a side view of the protector member of FIG. 24, in accordance with an aspect of the present invention.
Figure 27:
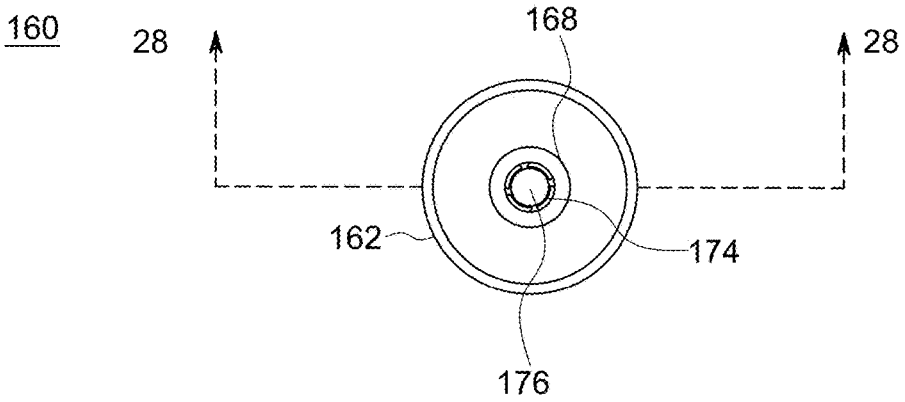
FIG. 27 is a first end view of the protector member of FIG. 24, in accordance with an aspect of the present invention.
Figure 28:
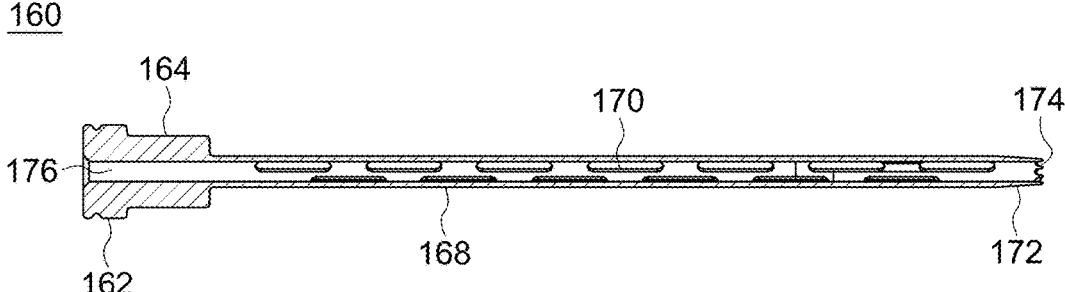
FIG. 28 is a cross-sectional view of the protector member of FIG. 24 taken along line 28-28 in FIG. 27, in accordance with an aspect of the present invention.
Figure 29:
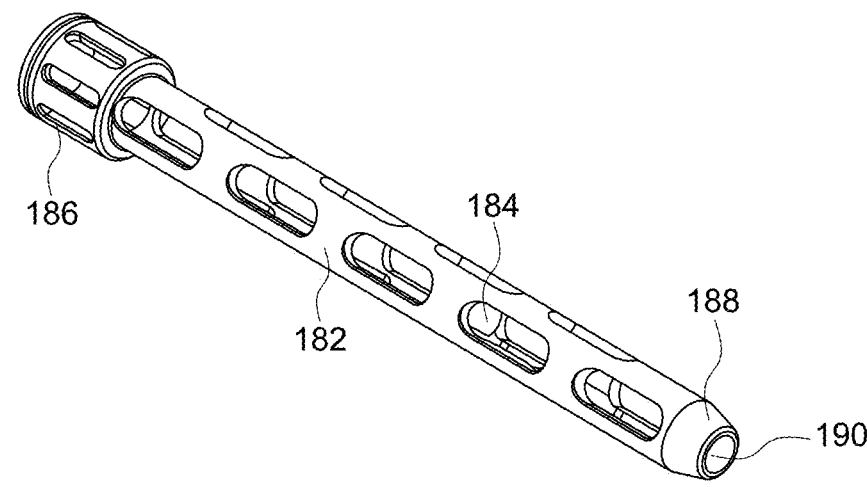
FIG. 29 is a first perspective view of the drill guide of the targeting guide of FIG. 1, in accordance with an aspect of the present invention.
Figure 30:
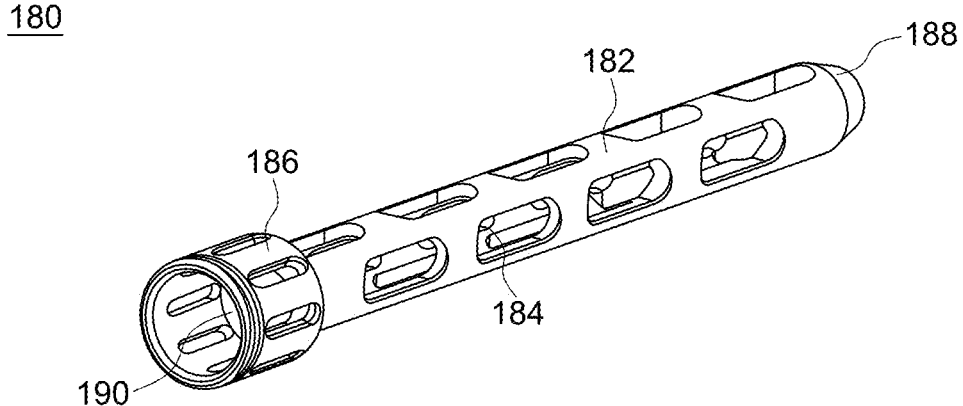
FIG. 30 is a second perspective view of the drill guide of FIG. 29, in accordance with an aspect of the present invention.
Figure 31:
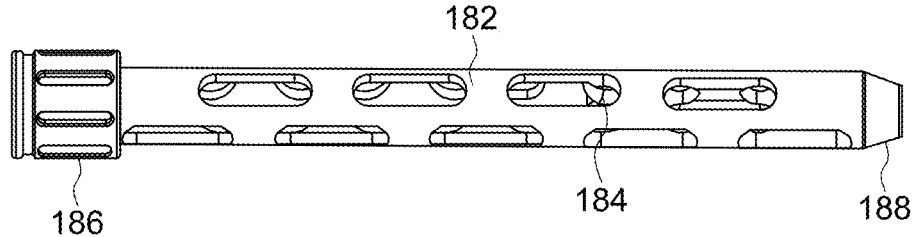
FIG. 31 is a side view of the drill guide of FIG. 29, in accordance with an aspect of the present invention.
Figure 32:
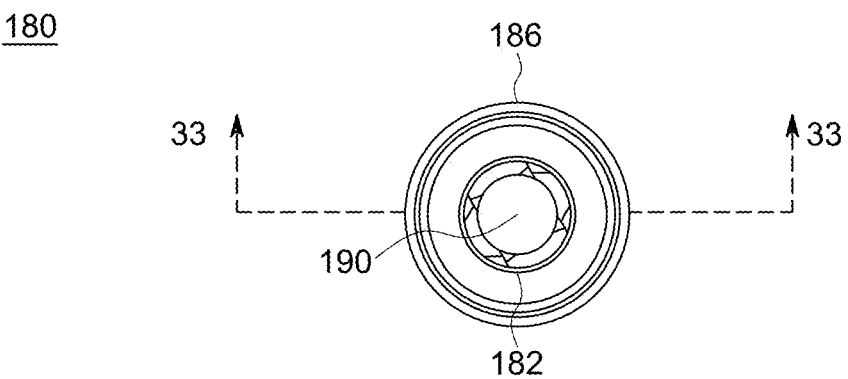
FIG. 32 is an end view of the drill guide of FIG. 29, in accordance with an aspect of the present invention.
Figure 33:
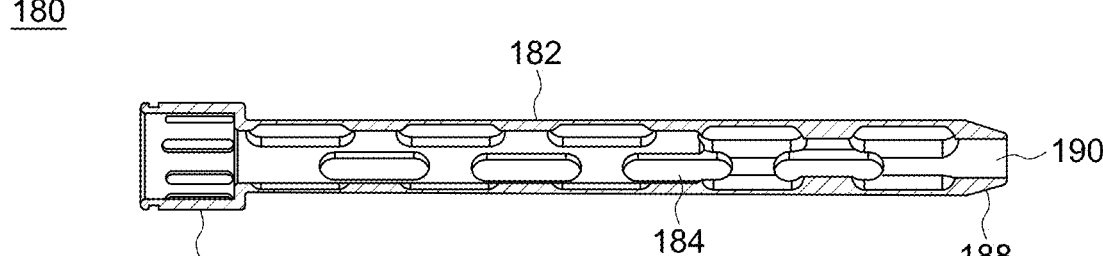
FIG. 33 is a cross-sectional view of the drill guide of FIG. 29 taken along line 33-33 in FIG. 32, in accordance with an aspect of the present invention.
Figure 34:
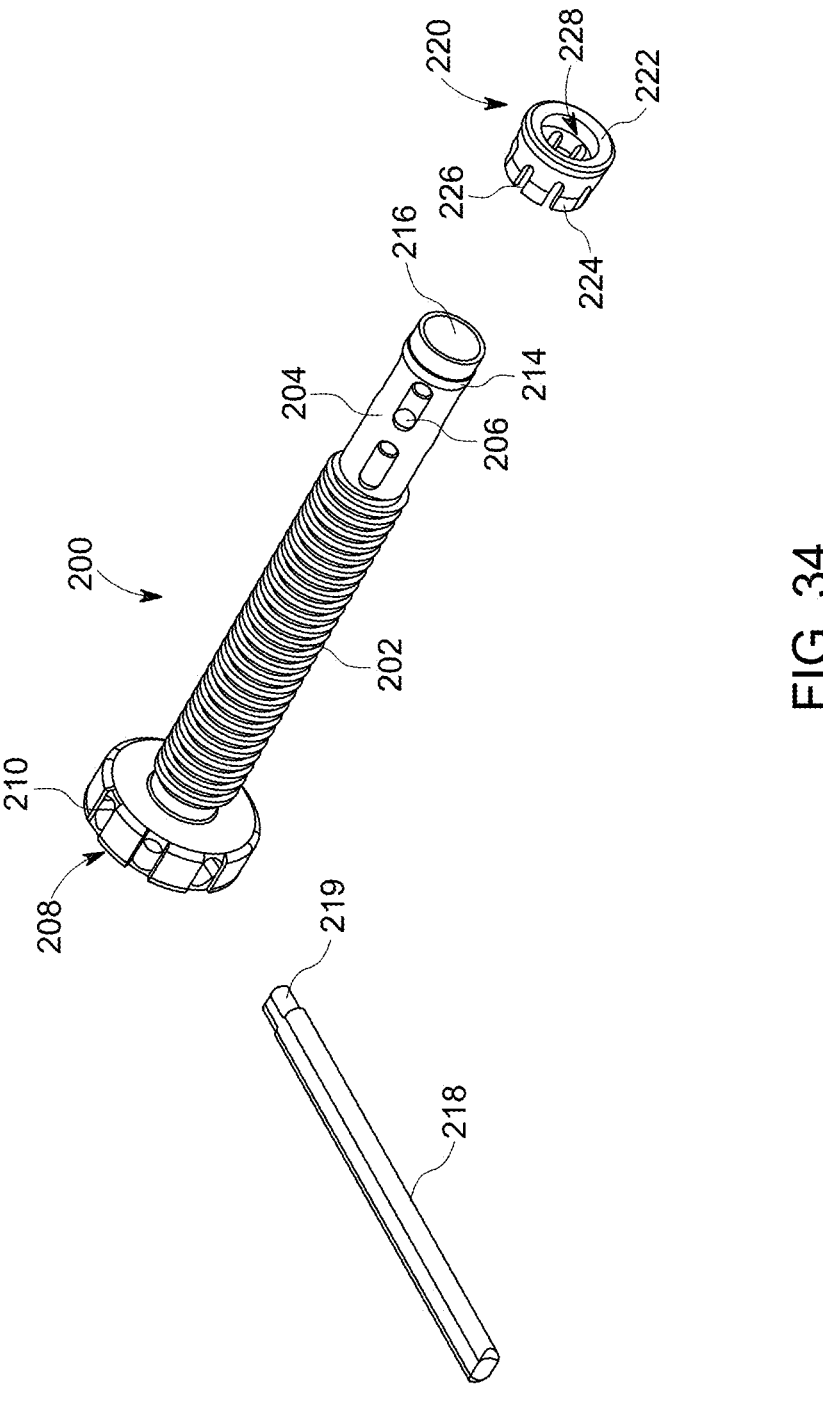
FIG. 34 is a first perspective view of the reduction guide tube, reduction cap and rotation tool of the targeting guide of FIG. 1, in accordance with an aspect of the present invention.
Figure 35:
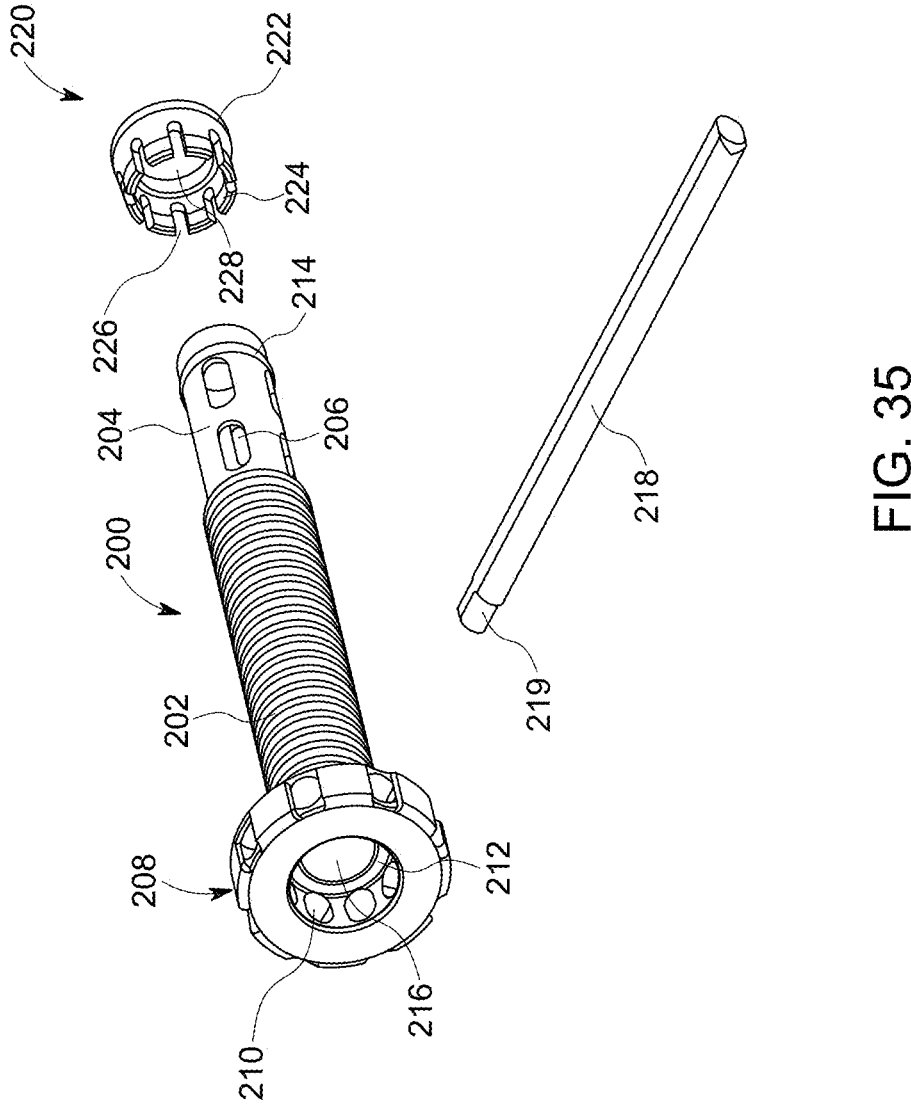
FIG. 35 is a second perspective view of the reduction guide tube and reduction cap of FIG. 34, in accordance with an aspect of the present invention.
Figure 36:
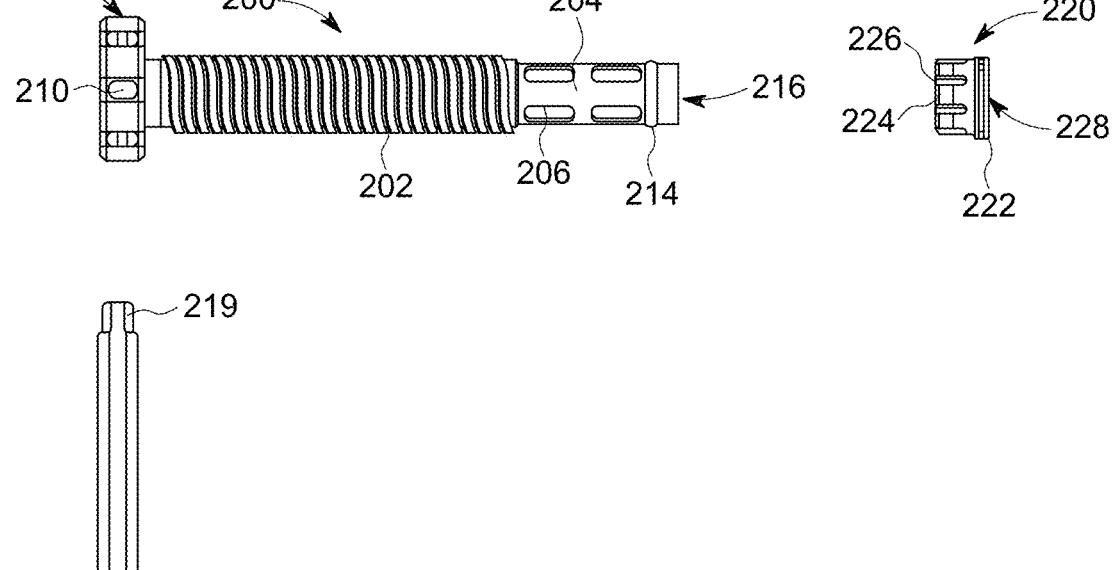
FIG. 36 is a top view of the reduction guide tube and reduction cap of FIG. 34, in accordance with an aspect of the present invention.
Figures 37, 38:
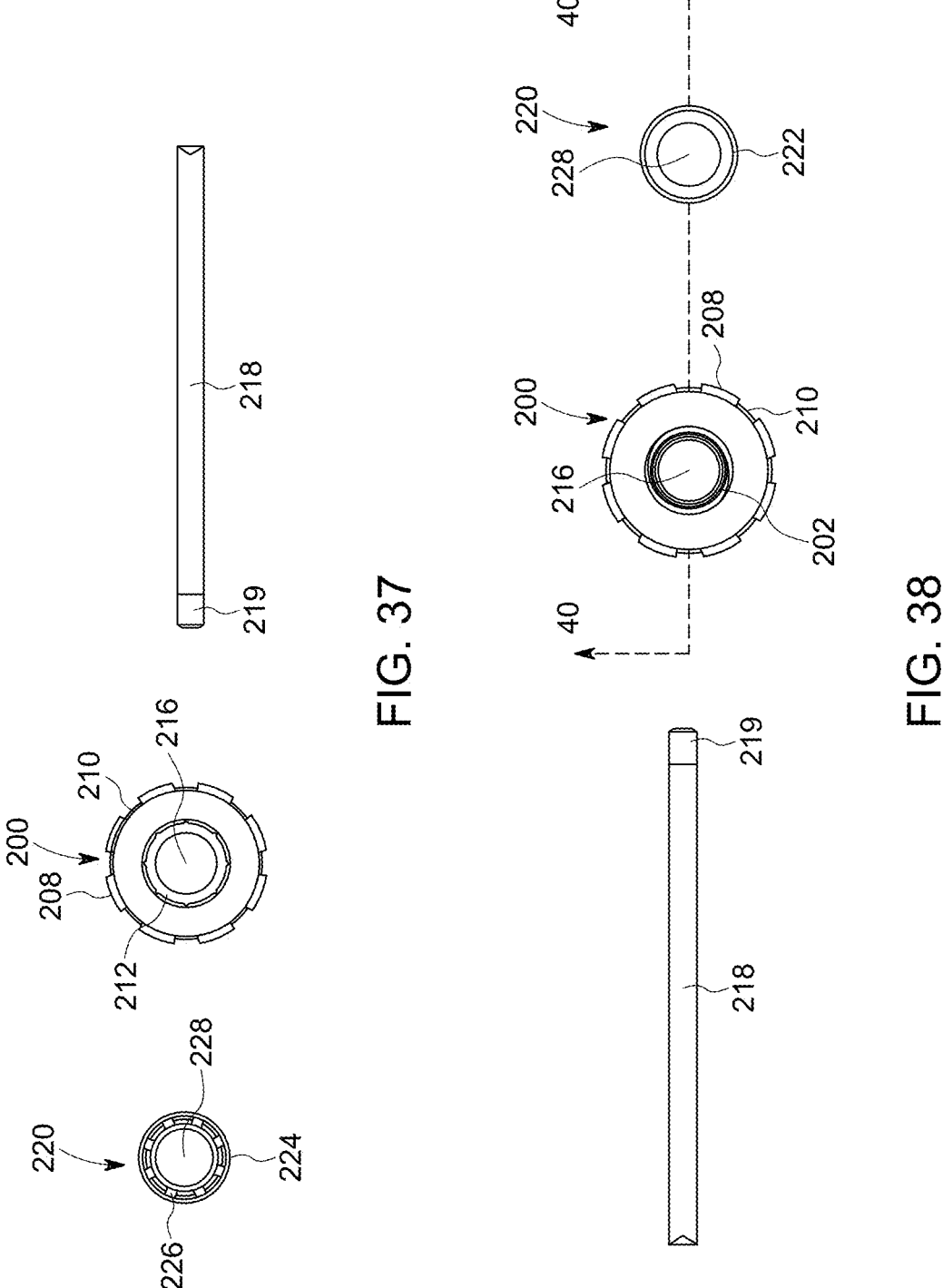
FIG. 37 is a first end view of the reduction guide tube and reduction cap of FIG. 34, in accordance with an aspect of the present invention.
FIG. 38 is a second end view of the reduction guide tube and reduction cap of FIG. 34, in accordance with an aspect of the present invention.
Figure 39:
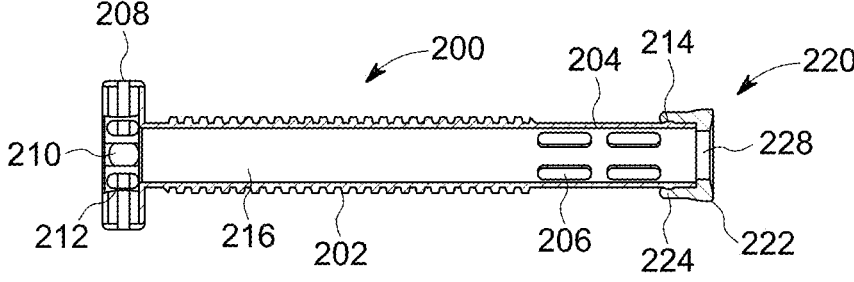
FIG. 39 is a cross-sectional view of the assembled reduction guide tube and reduction cap of FIG. 34 taken along line 39-39 in FIG. 5, in accordance with an aspect of the present invention.
Figure 40:
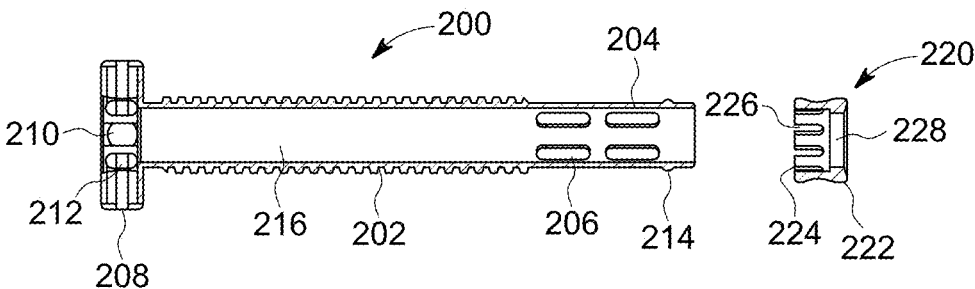
FIG. 40 is a cross-sectional view of the exploded reduction guide tube and reduction cap of FIG. 34 taken along line 40-40 in FIG. 38, in accordance with an aspect of the present invention.
Figure 41:
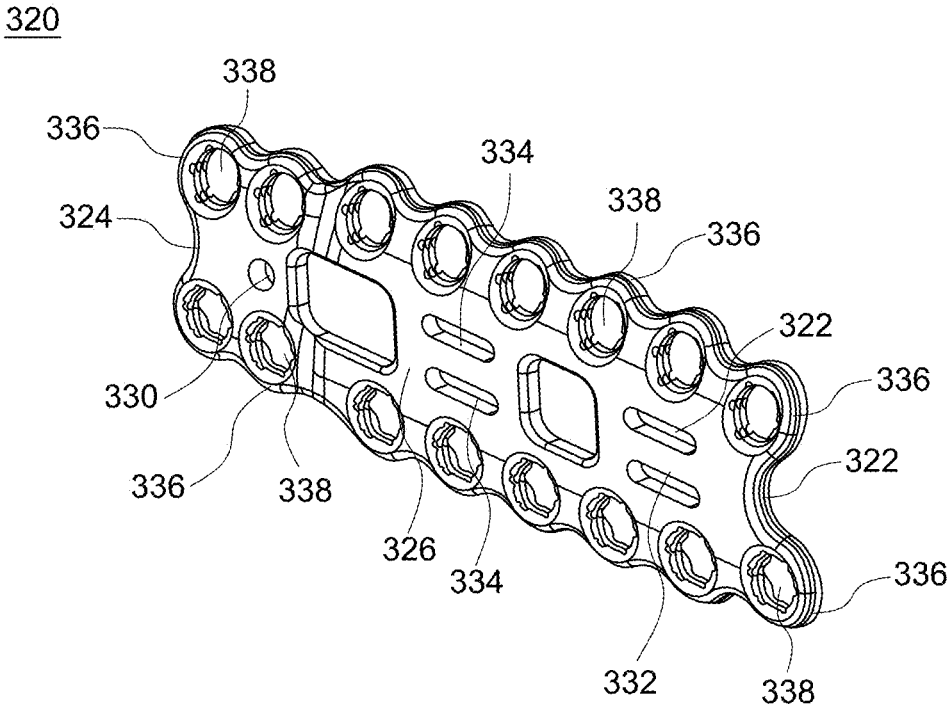
FIG. 41 is a first perspective view of the bone plate of FIG. 13, in accordance with an aspect of the present invention.
Figure 42:
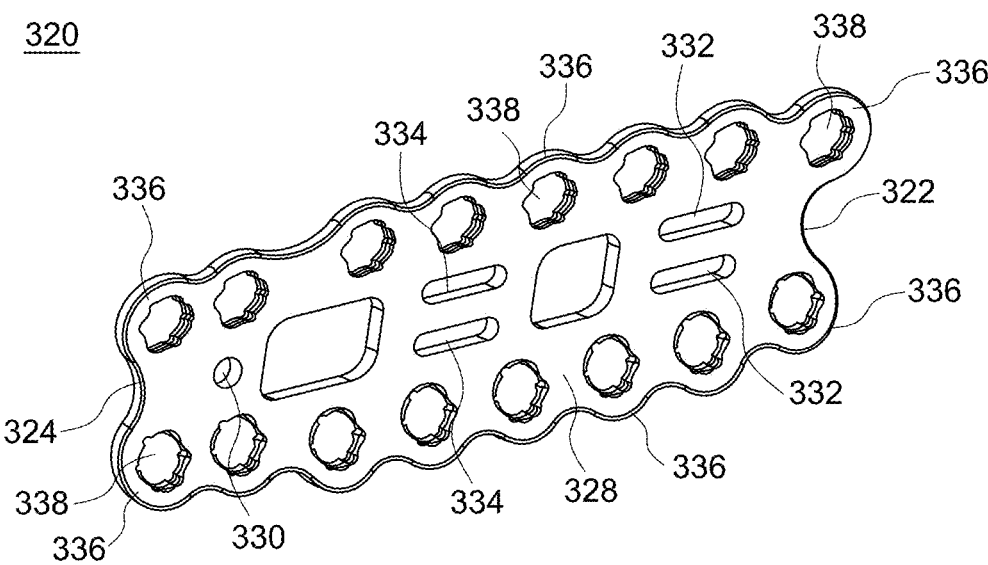
FIG. 42 is a second perspective view of the bone plate of FIG. 41, in accordance with an aspect of the present invention.
Figure 45:
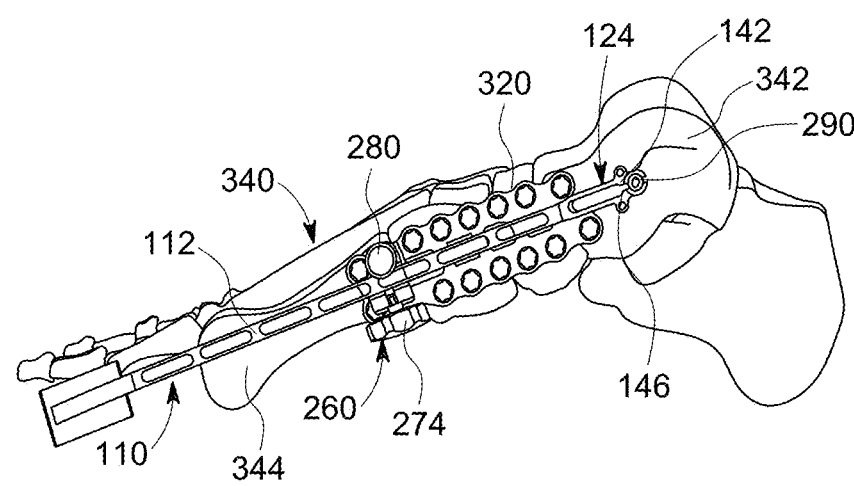
FIG. 45 is a medial view of the foot of FIG. 44 with the guide arm of FIG. 15 coupled to the implant holder and guide pin, in accordance with an aspect of the present invention.
Figure 46:
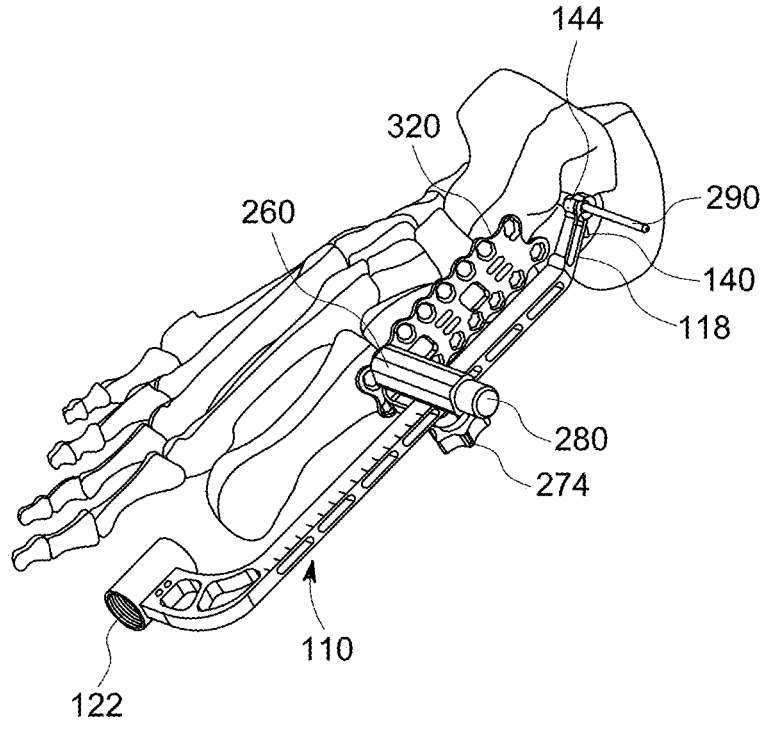
FIG. 46 is a dorsal perspective view of FIG. 45, in accordance with an aspect of the present invention.
Figure 47:
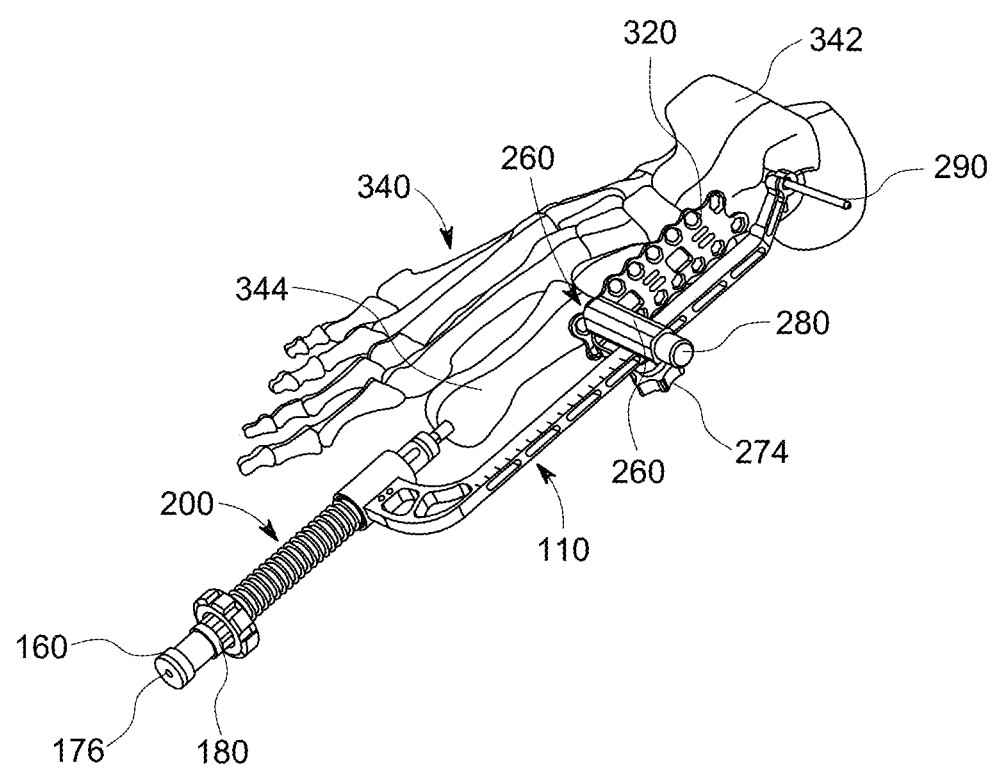
FIG. 47 is a dorsal perspective view of FIG. 46 with the reduction guide tube of FIG. 34 inserted into the guide arm, the drill guide of FIG. 29 inserted into the reduction guide tube, and the protector member of FIG. 24 inserted into the drill guide, in accordance with an aspect of the present invention.

Referring now to FIGS. 1-42, a targeting guide assembly 100 is shown. The targeting guide assembly 100 includes a guide arm 110, a target assembly 150, an implant holder 260, a guide pin 290, and anchoring wires 300, 310. The target assembly 150 may include a guide pin 152, a protector member 160, a drill guide 180, a reduction guide tube 200, and optionally a reduction cap 220, as shown in FIGS. 11-12. The reduction guide tube 200 may be received within the through hole 122 at a first end 114 of the guide arm 110. The implant holder 260 moveably engages the guide arm 110 and may, for example, slide along a body 112 of the guide arm 110 to allow for location adjustability of a coupled bone plate 320, as shown in FIGS. 45-47. The guide pin 290 rotatably couples to the second end 116 of the guide arm 110 and the anchoring wires 300, 310 are received within holes 142, 146 near the second end 116 of the guide arm 110.

As shown in FIGS. 15-23, the guide arm 110 includes a body or elongate body 112 connecting a first end 114 and a second end 116. The first end 114 may, for example, include a wider portion 120 that includes arcuate sides to attach the wider portion 120 in a generally perpendicular direction relative to the body 112. The wider portion 120 may also include a coupling portion 121 with a through hole 122 that is sized and shaped to receive the reduction guide tube 200. The through hole 122 may be, for example, larger or smaller than as shown in FIGS. 15-23. The through hole 122 may also be, for example, threaded along at least a portion of the hole 122. The through hole 122 may also be sized, for example, to correspond to the size of the threaded portion 202 of the reduction guide tube 200. The through hole 122 may extend along the wider portion 120 parallel to the body 112 allowing the target assembly 150 to extend parallel to the body 112 of the guide arm 110.

With continued reference to FIGS. 15-23, the second end 116 may, for example, include an angled portion 118. The angled portion 118 extends in a downward angled direction from the body 112 to the second end 116. A housing element 124 may be positioned at the second end 116 and may be configured or sized and shaped to receive the guide pin 290. The housing element 124 may include a first arm portion 130 and a second arm portion 132 separated by a channel 136. The channel 136 may extend from an exterior surface of the housing element 124 into the housing element 124 and into the angled portion 118. The housing element 124 may also include a top opening 126 and a bottom opening 128 forming an inner surface or cavity 134 extending between the top opening 126 and the bottom opening 128. The inner cavity 134 may intersect with the channel 136. The inner surface 134 may be, for example, configured or sized and shaped to allow the guide pin 290 to pivot, rotate, or move in multiple planes, as shown in FIGS. 6-8, 15-16, and 21-23. The top opening 126 may be, for example, sized to allow for insertion of a sphere 294 of the guide pin 290 into the housing element 124. The bottom opening 128 may be, for example, slightly smaller than the top opening 126 to capture or retain the guide pin 290 within the inner cavity 134 of the housing element 124. The housing element 124 may also include a first protrusion or ear 140 and a second protrusion or car 144, as shown in FIGS. 15, 16, and 20-23. The first protrusion 140 may extend out from the first arm 130 on a side opposite the channel 136 and the second protrusion 144 may extend out from the second arm 132 on a side opposite the channel 136. The first protrusion 140 may include a through hole 142. The through hole 142 may extend through the first arm 130, for example, at an angle. The second protrusion 144 may also include a through hole 146 and the through hole 146 may extend through the second arm 132 at an angle. The trajectories of the first through hole 142 and the second through hole 146 may be positioned, for example, for guide wires inserted into the through holes 142, 146 to converge without intersecting.

Figure 48:
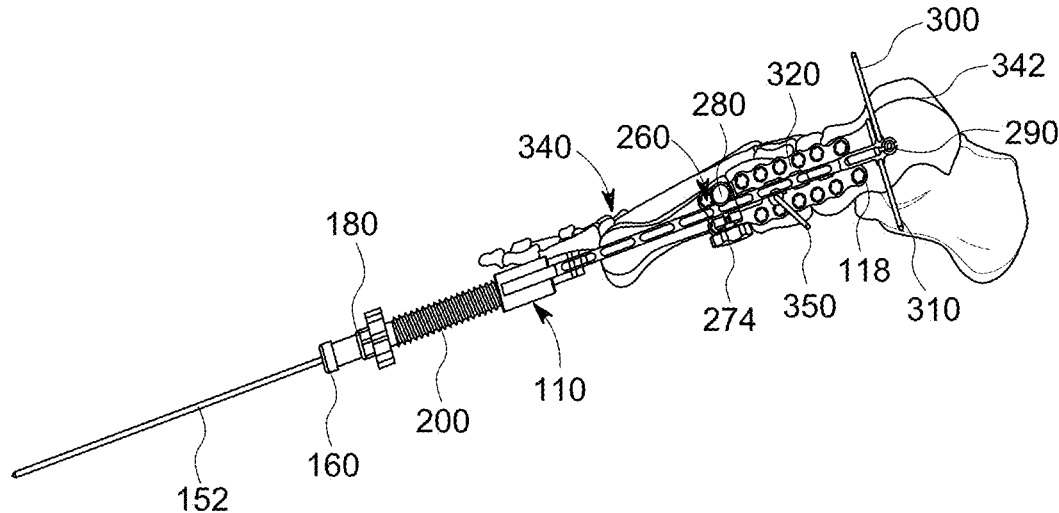
FIG. 48 is a medial view of the foot of FIG. 47 with a targeting pin inserted through the protector member and into the foot, two anchoring wires inserted through the guide arm and into the foot, and an olive wire inserted through the bone plate and into the foot, in accordance with an aspect of the present invention.
Figure 49:
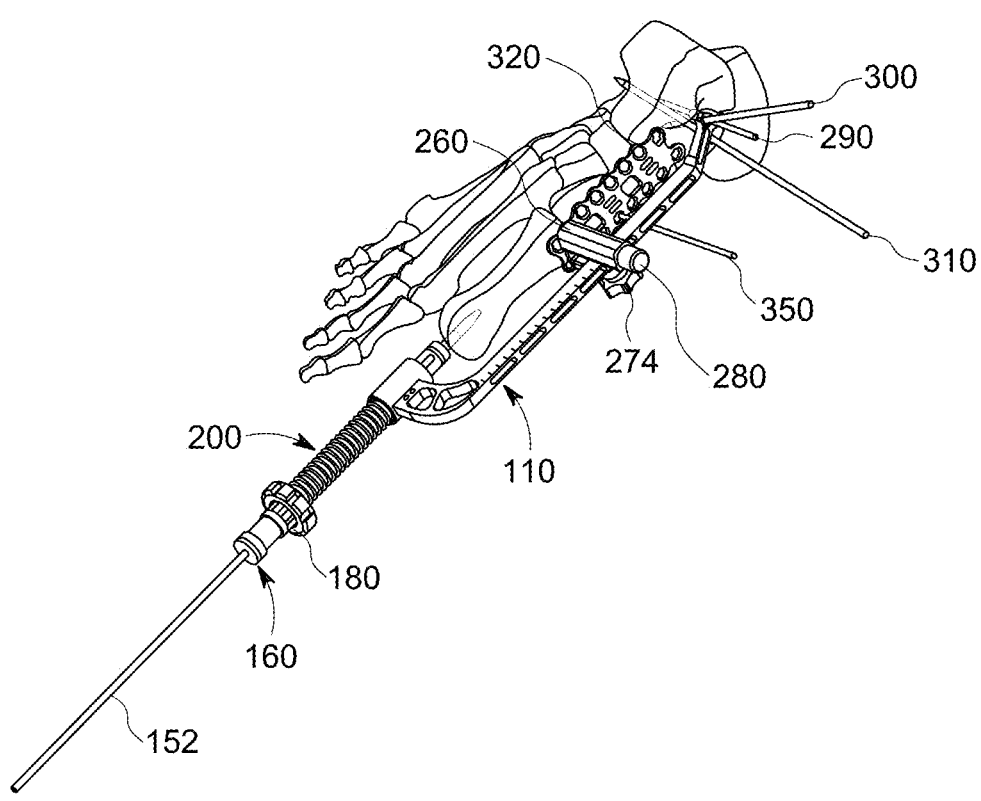
FIG. 49 is a dorsal perspective view of the foot of FIG. 48, in accordance with an aspect of the present invention.

With continued reference to the target assembly 150 of FIGS. 11-12, the guide pin or target pin 152 may include a first end or tip 154 for insertion into a patient and a second end 156 opposite the first end 154. The guide pin 152 may be, for example, a guide wire, k-wire, pin, or the like elongated pin like structure or member for insertion through a joint. In the depicted embodiment, the guide pin 152 has a smooth outer surface with a point or sharped portion 154 at one end. As shown in FIGS. 48-49, the guide pin 152 may be, for example, inserted from a distal to proximal direction through the cannulated opening or through hole 176 of the protector member 160 when placed or inserted into a bone pathway to secure the targeting guide at the surgical site and allow for the establishment of a target location proximally.

Referring now to FIGS. 9-12 and 24-28, the protector member 160 may include a knob or head 162 at a first end of a cylindrical portion, body portion or shaft 168. The head 162 may include an engagement portion 164 and a stopper portion 166. The engagement portion 164 may engage a recessed region in the drill guide tube 180 when inserted into the drill guide tube 180. The stopper portion 166 may contact the distal end of the drill guide tube 180 when inserted into the drill guide tube 180. The protector member 160 may include a tip 172 for contacting the patient's bone. The tip 172 may also include, for example, engagement teeth or ridges 174 to assist with engaging the patient's bone. The protector member 160 may further include a through hole or cannulated opening 176 extending through the protector member 160 along a longitudinal axis of the protector member 160. The body portion 168 of the protector member 160 may also include a plurality of openings 170 positioned along the length of the protector member 160. The openings 170 may extend from an exterior surface of the body portion 168 into the through hole 176. The protector member 160 may, for example, protect the surrounding soft tissue when the target pin 152 is inserted through the protector member 160 and into a patient's bones. As shown in FIGS. 1-4, 7-8, 13-14, 47-49, 51 and 52, the tip 172 of the protector member 160 may extend past the tip 188 of the drill guide tube 180 and the proximal end of the guide tube 200. The position of the tip 172 of the protector member 160 relative to the proximal ends of the drill guide 180 and the guide tube 200 provides greater visibility for anatomical location and improved anatomical trajectory on the surface of the bone.

As shown in FIGS. 9-12 and 29-33, the drill guide tube or drill guide 180 may include a cylindrical portion, body, or shaft 182 and a knob or head 186 positioned at a first end of the cylindrical portion 182. The drill guide 180 may also include a tip 172 positioned at the second end of the cylindrical portion 182. The cylindrical portion 182 of the drill guide 180 may have, for example, a larger diameter than the cylindrical portion 168 of the protector member 160. The drill guide 180 may also include a through hole or cannulated opening 190 extending along a longitudinal axis of the drill guide 180. The drill guide 180 may also include a plurality of openings 184 positioned along the length of the cylindrical portion 168. The openings 184 may extend from an exterior surface of the body portion 168 into the through hole 190. The drill guide 180 may, for example, protect the surrounding soft tissue when a drill is inserted through the cannulated opening 190 to drill an opening for inserting the threaded member 240.

The reduction guide tube 200 may include a threaded portion 202, a body 204 extending away from a first or distal end of the threaded portion 202, and a head 208 coupled to the second or proximal end of the threaded portion 202, as shown in FIGS. 9-12, 34-36, 39 and 40. The guide tube 200 may also include a through hole 216 extending along the longitudinal axis of the guide tube 200 through the head 208, threaded portion 202 and the body 204. The body 204 may include, for example, a plurality of openings 206 positioned along the length of the body 204 and extending from an exterior surface of the body 204 into the through hole 216. The body 204 may also include a lip or protrusion 214 positioned near the first end and extending out from the exterior surface of the body 204. The lip 214 may circumferentially surround the body 204. The head 208 may include cutouts or recesses 210 positioned around the exterior surface of the head 208. The cutouts 210 may be generally perpendicular to the through hole 216. The cutouts 210 may be, for example, sized and shaped to receive the engagement tab or protrusion 219 of the tool, instrument, handle, Tommy Bar tool 218. The tool 218 may be used to rotate the guide tube 200 and translate the guide tube 200 with respect to the through hole 122 of the guide arm 110. The head 208 may also include a recessed opening 212 extending into the guide tube 200 from the second end toward the first end. The recessed opening 212 may be positioned, for example, around or to surround the through hole 216. The recessed opening 212 may be, for example, sized and shaped to receive the knob 186 of the drill guide 180. The body 204 may have a first diameter, the threaded portion 202 may have a second diameter, and the head 208 may have a third diameter. As shown, the second diameter may be, for example, larger than the first diameter and the third diameter may be, for example, larger than the first and second diameter.

With continued reference to FIGS. 9-12, 34-36, 39, the reduction cap or compression cap 220 is shown. The reduction cap 220 may include a base portion 222 and a plurality of tabs or protrusions 224 extending away from a first or proximal end of the base portion 222. The reduction cap 220 may also include a through hole 228 extending through the base portion 222 and between the plurality of tabs 224 along a longitudinal axis of the reduction cap 220. Each of the plurality of tabs 224 may include a tooth 230 extending out from an interior surface of the tabs 224 and into the through hole 228. The plurality of teeth 230 may be, for example, sized and shaped to engage the lip 214 of the guide tube 200. The plurality of tabs 224 may also be separated by a plurality of grooves 226 extending from the proximal end of the reduction cap 220 towards the base portion 222. The reduction cap 220 may also include, for example, a slot (not shown) extending from the first or proximal end of the reduction cap 220 to the second or distal end of the reduction cap 220 and from an exterior surface of the reduction cap 220 into the through hole 216. The slot (not shown) may allow for the reduction cap 220 to be removed from the targeting guide 100 while the target pin 152 is inserted into a patient's foot.

The threaded member or implant 240 may include a head portion 242 and a shaft 246, as shown in FIGS. 1-4 and 7-14. The head portion 242 may be positioned at a first end of the shaft 246 and cutting flutes or distal cutting flutes 248 may be positioned at a second end of the shaft 246. The threaded member 240 may also include proximal cutting flutes 244 positioned on the head portion 242. The cutting flutes 244, 248 may facilitate the insertion of the threaded member 240 into bones. In addition, the threaded member 240 may include a through hole or cannulated opening 250 extending through the threaded member 240 along a longitudinal axis. The through hole 250 may be configured or sized and shaped to receive the target pin 152. Alternatively, the threaded member 240 may be, for example, solid without a longitudinal opening. As shown, the threaded member 240 is threaded along the entire length, however, it is also contemplated that the threaded member 240 may be threaded along only a portion, for example, having partially or segmentally divided threads along the length.

The implant holder 260 may include a housing 262, a knob 274 and a locking member 280. The housing 262 may include an attachment arm 264 extending from and parallel to the housing 262 to form, for example, a U-shaped or hook like structure. The attachment arm 264 hooks under the bottom of the body 112 of the guide arm 110 to permit the sliding movement along the longitudinal axis of the body 112. A channel 266 is formed between the attachment arm 264 and the housing 262 and may be configured or sized and shaped to receive the body 112 of the guide arm 110. The attachment arm 264 may also include at least one hole 268 extending through the attachment arm 264 from an exterior surface into the channel 266. The at least one hole 268 may be, for example, one to four holes and more particularly three holes. The implant holder 260 may also include an alignment post 270 extending away from a bottom surface of housing 262. The implant holder 260 may further include a through hole 272 extending through the housing 262 from a top surface to a bottom surface adjacent to the alignment post 270. The knob 274 may include an engagement protrusion 276 extending away from a back surface of the knob 274. The engagement protrusion 276 may be, for example, threaded to engage the at least one hole 268 of the attachment arm 264 to secure the implant holder 260 to the body 112 of the guide arm 110 at the desired position. The locking member 280 may include a shaft 282 with a knob 284 at a first end and a threaded portion 286 at a second end. The shaft 282 may be inserted through the through hole 272 of the housing 262 until the knob 284 contacts a top surface of the housing 262 and the threaded portion 286 extends past the bottom surface of the housing 262. The threaded portion 286 may engage a bone plate, such as bone plate 320, as described in greater detail below. The knob 284 may be rotated to insert the threaded portion 286 into the bone plate 320 and to remove the threaded portion 286 from the bone plate 320.

As shown in FIGS. 1-4 and 6-14, the guide pin 290 includes a shaft 292, a sphere 294, a tip 296, and a cylindrical protrusion 298. The sphere or spherical member 294 may be positioned between a first end and the tip 296. The tip 296 is threaded, however, it is also contemplated that the tip 296 may also have a smooth outer surface to facilitate insertion. The tip 296 is configured or sized and shaped to allow for the user to insert the guide pin 290 into a target bone either directly or through the skin. Once inserted into the target bone, the guide pin 290 may be secured to establish the target location for the threaded member 240. The sphere 294 is sized and shaped or configured to be inserted into the housing element 124 to allow for a full range of pivoting motions, as shown in FIGS. 1-4, 6, 50 and 52. The cylindrical protrusion 298 may be positioned adjacent to the sphere 294 and more specifically, between the sphere 294 and the tip 296.

As shown in FIGS. 1-14, the targeting guide 100 may also include a first anchoring wire 300 and a second anchoring wire 310. The first anchoring wire 300 includes a first end 302 and a second end or tip 304 positioned opposite the first end 302. The second anchoring wire 310 includes a first end 312 and a second end or tip 314 positioned opposite the first end 312. The anchoring wires 300, 310 may be inserted through the through holes 142, 146 of the first and second protrusions 140, 144 and into a patient's foot.

Referring now to FIGS. 13-14 and 41-42, a bone plate 320 is shown. The bone plate 320 has a first or proximal end 322 opposite a second or distal end 324 and a top or external surface 326 opposite a bottom or bone contacting surface 328. The bone plate 320 may include a locking member opening 330 positioned near the second end 324. The locking member opening 330 receives the threaded portion 286 of the locking member 280 to secure the bone plate 320 to the implant holder 260. The bone plate 320 may also include proximal channels or openings 332 positioned near the first end 322 and intermediate channels or openings 334 positioned near a midpoint of the bone plate 320. The bone plate 320 further includes a plurality of lobes 336 positioned on the sides and ends of the bone plate 320. Each of the lobes 336 of the plurality of lobes 336 may include an opening or bone screw opening 338. The bone screw openings 338 may receive bone fasteners or screws to secure the bone plate 320 to a patient's foot.

The targeting guide assembly 100 may be assembled by inserting the guide pin 290 into the housing element 124 of the guide arm 110. Alternatively, the housing element 124 of the guide arm 110 may be inserted over the guide pin 290. The reduction guide tube 200 may be inserted into the through hole 122 of the guide arm 110. The drill guide 180 may then be inserted into the through hole 216 of the guide tube 200. Next, the protector member 160 may be inserted into the through hole 190 of the drill guide 180 to receive the target pin 152. Alternatively, the protector member 160 may be inserted into the drill guide 180 and the combined protector member 160 and drill guide 180 may be placed into the reduction guide tube 200. In addition, the implant holder 260 may be aligned with the body 112 of the guide arm 110 and secured in the desired position by engaging the engagement protrusion 276 of the knob 274 with the body 112 of the guide arm 110. The locking member 280 may be inserted into the opening 272 of the housing 262. Then, the alignment post 270 may be aligned with a corresponding alignment opening (not shown) in the bone plate 320 and the threaded portion 286 of the locking member 280 may engage a corresponding threaded opening 330 in the bone plate 320.

Figure 43:
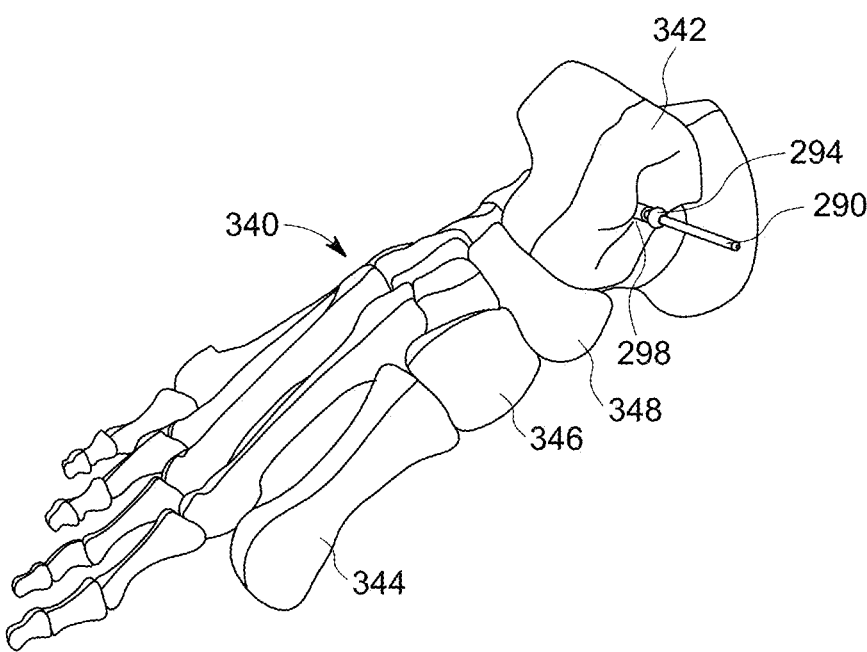
FIG. 43 is a dorsal perspective view of a portion of a foot with the guide pin of the targeting guide of FIG. 1 inserted into the foot, in accordance with an aspect of the present invention.
Figure 44:
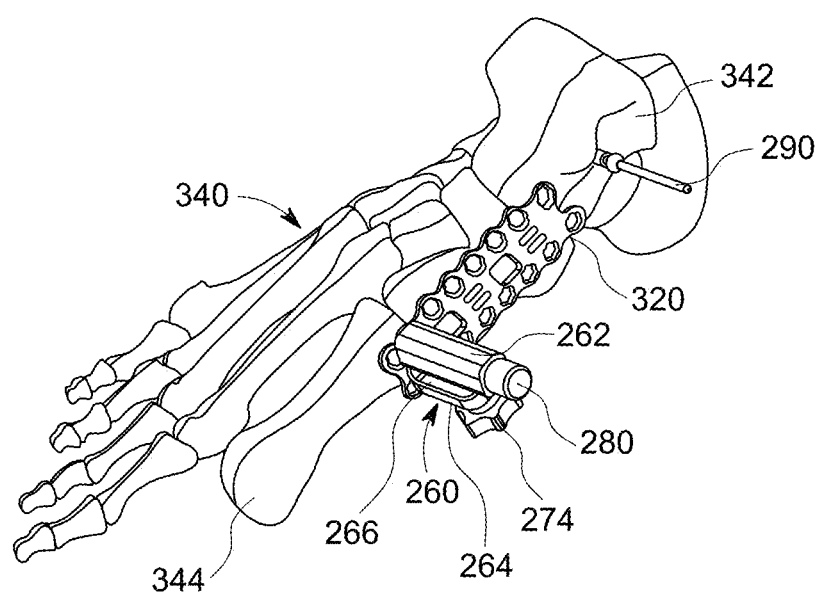
FIG. 44 is a dorsal perspective view of the foot of FIG. 43 with the bone plate of FIG. 41 positioned on the foot and an implant holder of the targeting guide of FIG. 1 coupled to the bone plate, in accordance with an aspect of the present invention.

Referring now to FIGS. 43-58, a method for using the targeting guide assembly 100 to correct bone deformities is shown. The method may include, for example, performing an arthrodesis across at least one joint. The at least two bones of the at least one joint may be positioned in a desired final position and may be temporarily fixed. As shown in FIG. 43, the method may also include inserting a guide pin 290 into a first bone 342 to set the trajectory for the target pin 152 and the threaded member 240. The first bone 342 may be, for example, the talus, specifically, the neck of the talus. Next, as shown in FIG. 44, a bone plate 320 may be selected and the implant holder 260 may be coupled to the locking member opening 330 with the locking member 280. The knob 274 may be coupled to the attachment arm 264 of the implant holder 260 before or after the implant holder 260 is coupled to the bone plate 320. The housing element 124 of the guide arm 110 may then be coupled to the sphere 294 of the guide pin 290, as shown in FIGS. 45-46. The guide arm 110 may be rotated about the sphere 294 to position the first end 114 of the guide arm 110 with respect to a second bone 344. The second bone 344 may be, for example, the first metatarsal. The guide arm 110 may be inserted into the channel 266 of the implant holder 260 as the guide arm 110 is pivoted on the sphere 294, to position the bone plate 320 and the distal portion of the guide arm 110 over the head of the second bone 344. Once the bone plate 320 is coupled to the implant holder 260, the position of the bone plate 320 may be adjusted along the length of the guide arm 110 to allow for bone plate 320 positioning in a first plane, for example, the sagittal plane. The guide arm 110 may alternatively or in addition to adjustment along the length be rotated around the guide pin 290 to rotate the bone plate 320 in a second plane, for example, the frontal plane. Movement of the bone plate 320 in the two planes allows for fixation devices or bone screws 352 to be inserted with a trajectory to avoid contacting the target pin 152 and/or threaded member 240. After the desired position and trajectory are achieved, the knob 274 of the implant holder 260 may be tightened to secure the guide arm 110 to the implant holder 260.

Referring now to FIG. 47, the reduction guide tube 200, the drill guide 180 and the protector member 160 of the target assembly 150 may be placed to locate the starting point of the target pin or beaming screw guide wire 152. For example, the reduction guide tube 200 may be inserted into the through hole 122 engaging the threaded portion 202 of the guide tube 200 with the threads extending through the through hole 122 of the guide arm 110. Next, the drill guide 180 may be inserted into the through hole 216 of the guide tube 200 until the knob 186 of the drill guide 180 is positioned in the recessed opening 212 of the guide tube 200. Then, the protector member 160 may be inserted into the through hole 190 of the drill guide 180. The target pin 152 may then be inserted into the through hole 176 of the protector member 160 and into at least one bone 342, 344, 346, 348, as shown in FIGS. 48-49. The target pin 152 will be inserted, for example, first through the metatarsal head 344. The trajectory of the target pin 152 will overlap, intersect or engage the guide pin 290. In one embodiment, the implant holder 260 may be coupled to the guide arm 110 before the guide arm 110 is coupled to the guide pin 290. Alternatively, the implant holder 260 may be coupled to the guide arm 110 after the target pin 152 is inserted into the bones 342, 344, 346, 348. In an alternative embodiment, the bone plate 320 may now be coupled to the implant holder 260 and aligned on the bones 342, 344, 346, 348.

Figure 50:
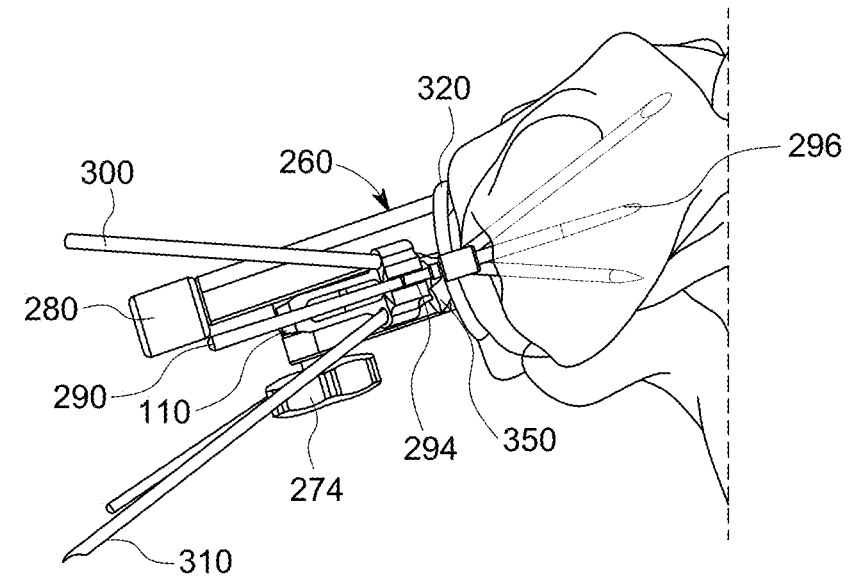
FIG. 50 is an enlarged view of the proximal end of the guide arm on the foot of FIG. 49, in accordance with an aspect of the present invention.
Figure 51:
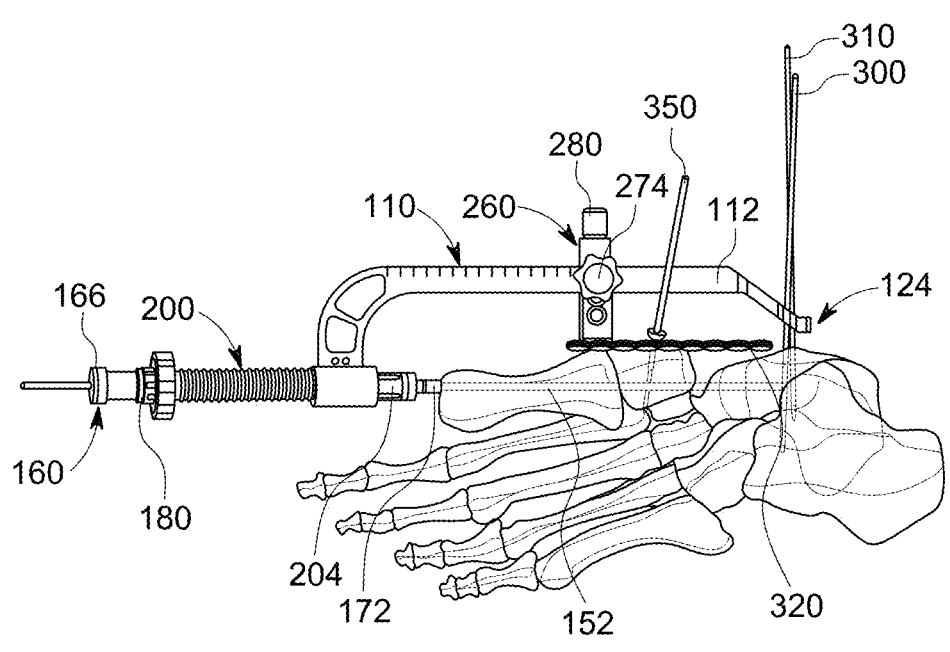
FIG. 51 is a plantar view of the foot of FIG. 49, in accordance with an aspect of the present invention.
Figure 52:
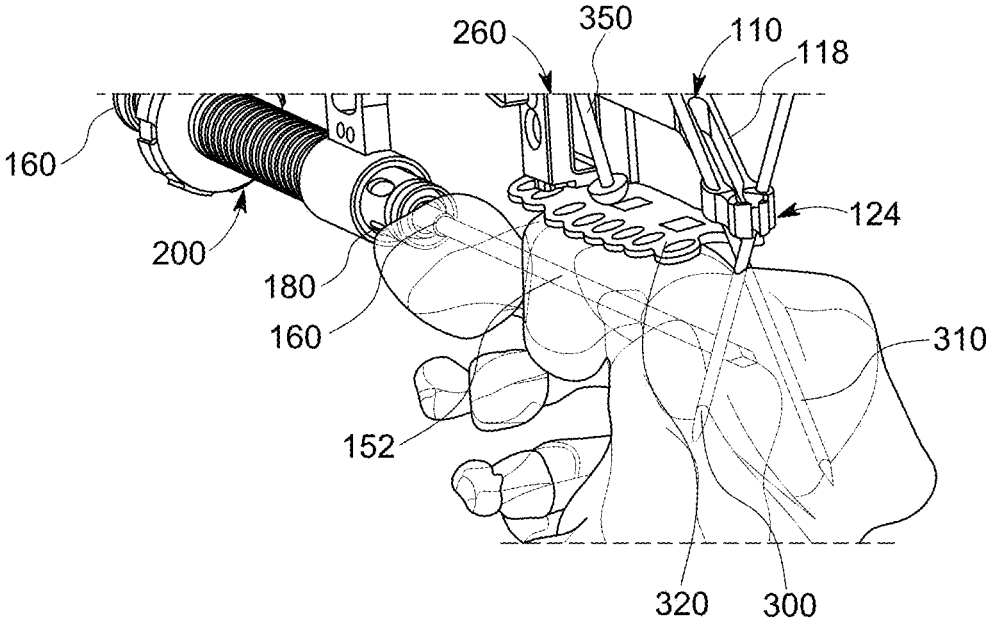
FIG. 52 is an enlarged plantar perspective view of a portion of the foot of FIG. 49 with transparent bones, in accordance with an aspect of the present invention.

After the target pin 152 is placed in the desired position and confirmed on fluoroscopy, two anchoring wires or k-wires 300, 310 may be inserted into the first bone 342, as shown in FIGS. 48-50. The anchoring wires 300, 310 may alternatively be inserted after the initial placement of the guide wire 152 into the metatarsal and prior to joint reduction. The wires 300, 310 may be inserted through the through holes 142, 146 in the protrusions 140, 144 of the guide arm 110 and into the first bone 342 to provide additional stability. As shown in FIGS. 48-52, an olive wire 350 may also be inserted through an opening 338 in the bone plate 320 and into the third bone 346, for example, the medial cuneiform, to secure the bone plate 320 to the foot 340. Next, the guide pin 290 may be removed from the first bone 342 and the housing element 124 of the guide arm 110, as shown in FIGS. 51-52. Once the guide pin 290 is removed, the target pin 152 may be advanced into the talus or talar body 342 through the entire first metatarsal 344, the medial cuneiform 346 and the navicular bone 348, as shown in FIGS. 51-52. The guide pin 290 may be inserted beyond the anchoring wires 300, 310 as the trajectory of the guide pin 290 extends between the two anchoring wires 300, 310.

Figure 53:
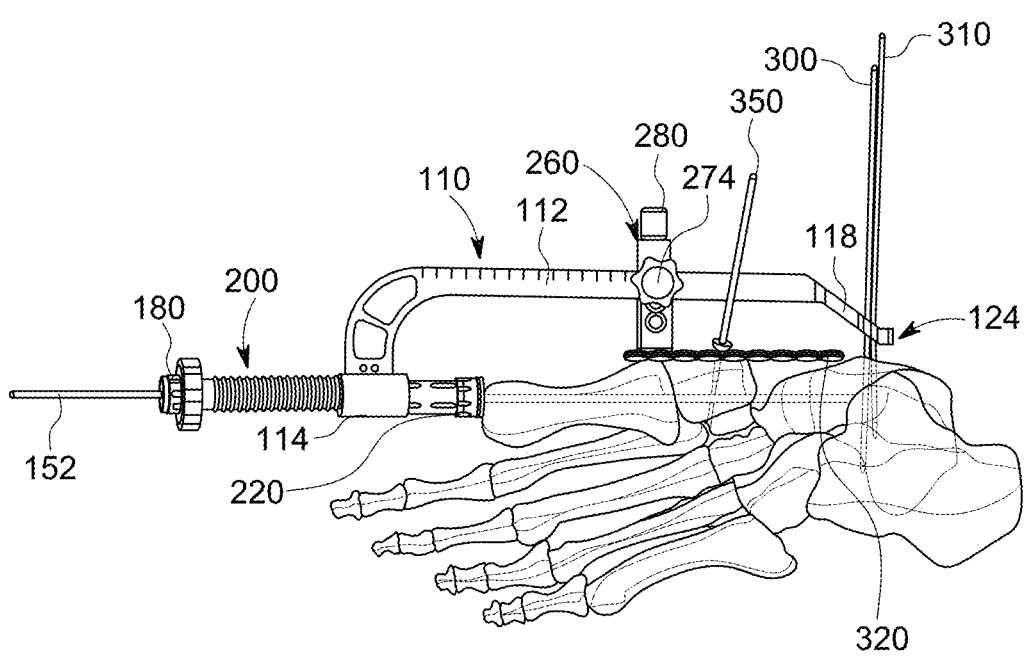
FIG. 53 is a plantar view of the foot of FIG. 49 with a reduction cap coupled to the reduction guide tube and the protector member removed, in accordance with an aspect of the present invention.
Figure 54:
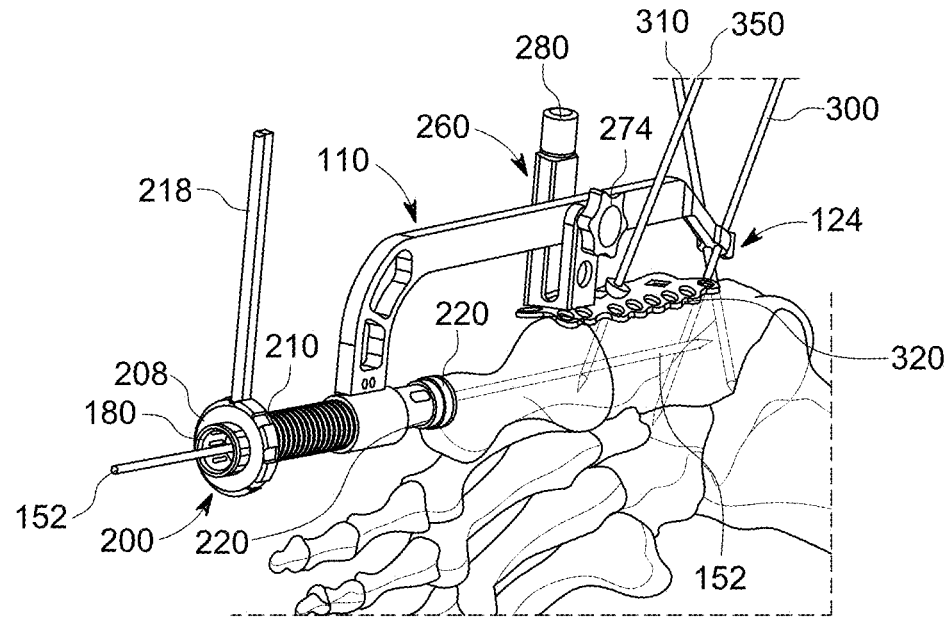
FIG. 54 is a plantar perspective view of the foot of FIG. 53, in accordance with an aspect of the present invention.

Referring now to FIGS. 53-54, the protector member 160 may be removed from the drill guide 180 after the guide pin 290 is inserted through the bones 342, 344, 346, 348. The protector member 160 may be removed by sliding the protector member 160 out of the through hole 190 of the guide arm 180 over the target pin 152. Next, a compression cap 220 may optionally be coupled to the proximal end of the reduction guide tube 200. Although not shown, the compression cap 220 may include a slit to allow for placement of the compression cap 220 onto the guide tube 200 with the target pin 152 extending through the through hole 216 of the guide tube 200. After removal of the protector member 160, with or without the coupled compression cap 220, joint reduction may be performed by rotating the head 208 of the reduction guide tube 200, for example, in a clockwise direction. If additional torque is needed to perform the reduction, the tool 218 may be used by inserting the engagement tab 219 of the tool 218 into the cutouts 210 in the head 208 of the tool 218 and rotating the head 208, as shown in FIG. 54.

Figure 55:
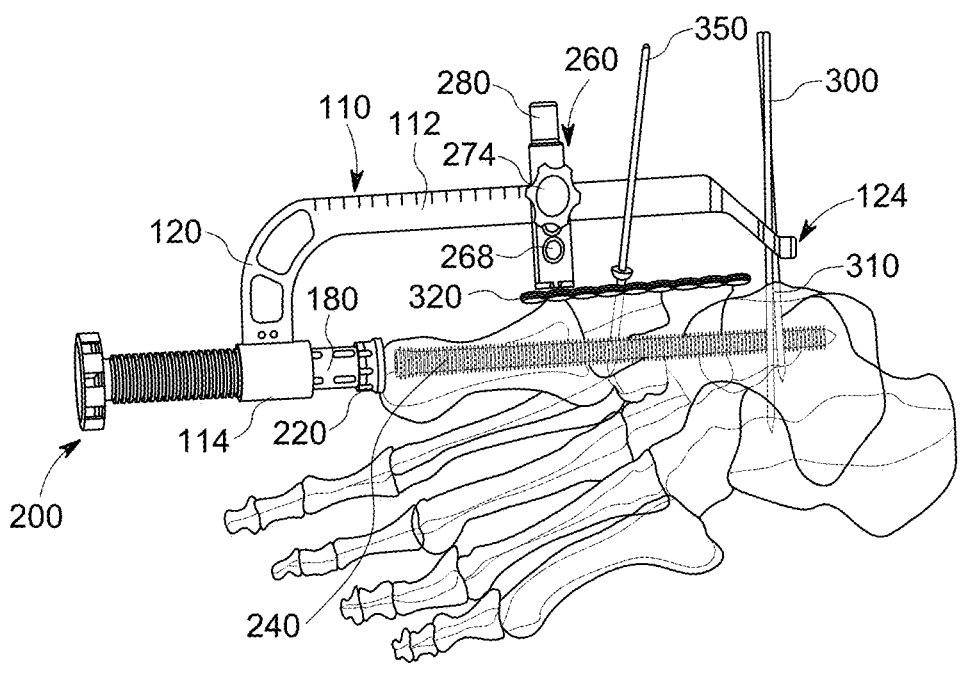
FIG. 55 is a plantar perspective view of the foot of FIG. 54 after removal of the drill guide, insertion of the threaded member, and removal of the targeting pin, in accordance with an aspect of the present invention.
Figure 56:
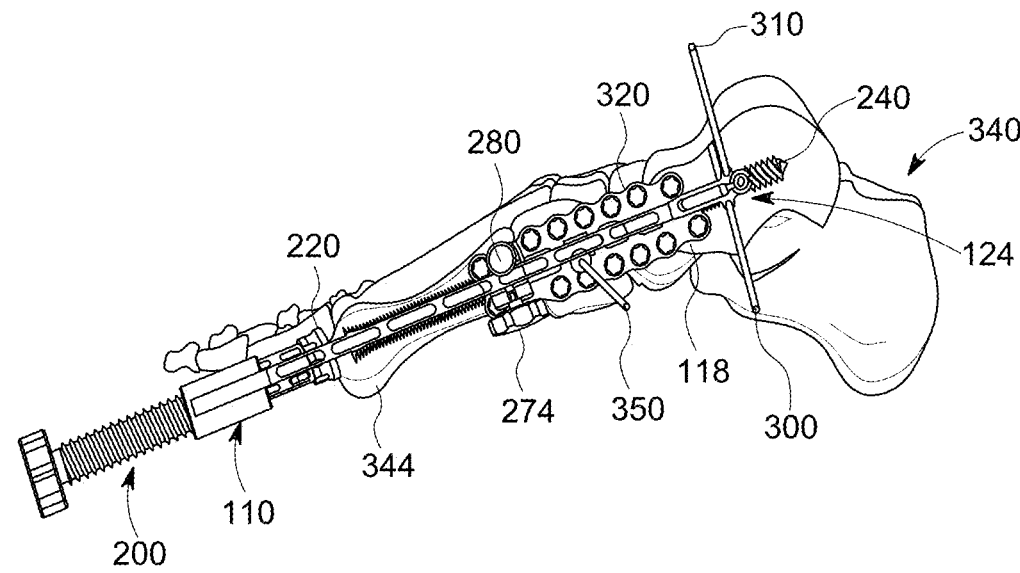
FIG. 56 is a medial view of the foot of FIG. 55, in accordance with an aspect of the present invention.
Figure 57:
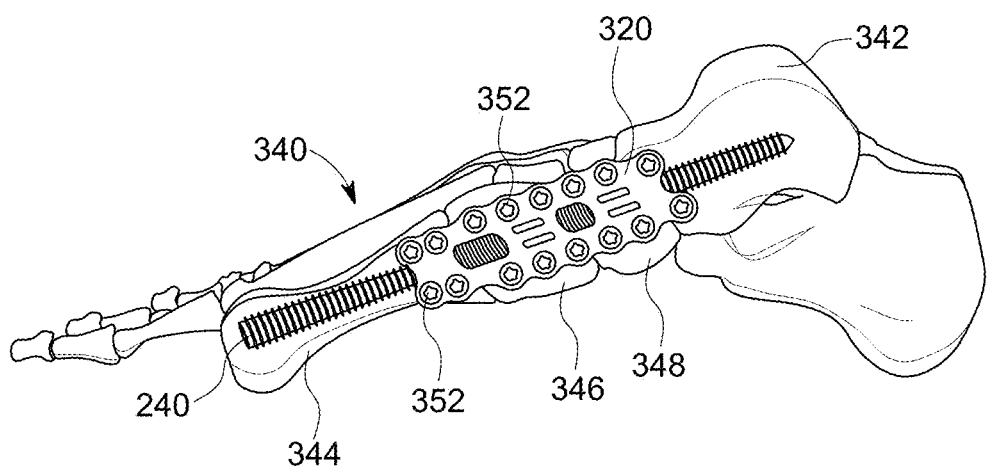
FIG. 57 is a medial view of the foot of FIG. 56 after insertion of bone fasteners through the bone plate and into the foot, removal of the anchoring wires, olive wire, guide arm, reduction guide tube, reduction cap, implant holder, and guide pin, in accordance with an aspect of the present invention.
Figure 58:
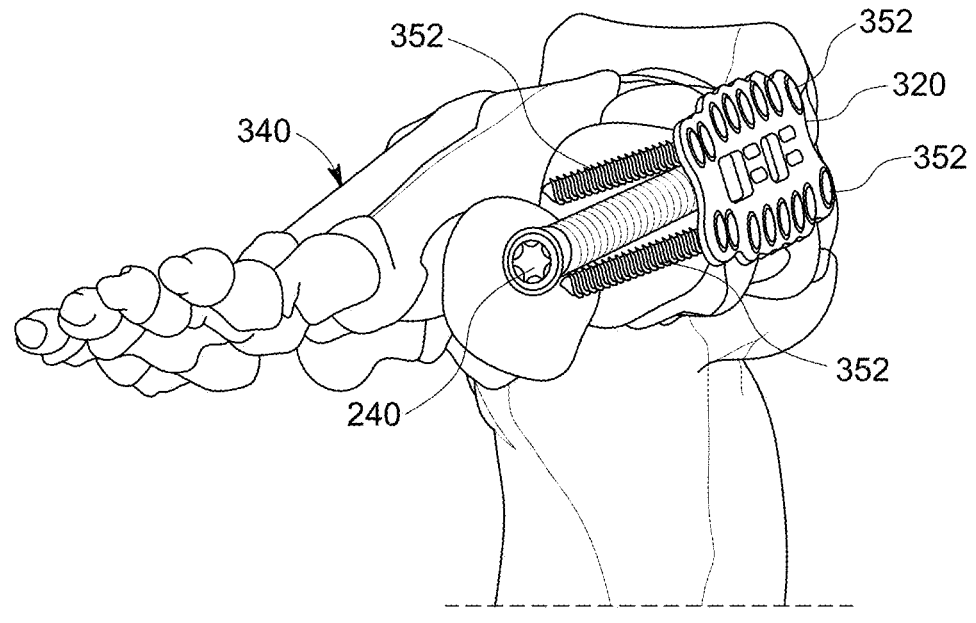
FIG. 58 is a distal perspective view of the foot of FIG. 57, in accordance with an aspect of the present invention.

A cannulated drill may optionally be used to drill through the drill guide 180 and over the target pin 152. A countersink may also optionally be drilled through the drill guide 180. Next, the cannulated drill and drill guide 180 may then be removed from the reduction guide tube 200. The threaded member 240 may then be inserted over the target pin 150, through the guide tube 200 and into the bones 342, 344, 346, 348, as shown in FIGS. 55-56. Next, at least one olive wire 350, more preferably at least two olive wires 350, may be placed into the channels 332, 334 of the bone plate 320 to maintain the position of the plate 320. The olive wires 350 inserted into channels 332, 334, allows for the surgeon to slide the plate 320 in a proximal-distal direction for proper placement. Next, as shown in FIGS. 57-58, the reduction guide tube 200, the anchoring wires 300, 310, the guide arm 110, the implant holder 260, and the target pin 152 may be removed from the foot 340 and surgical field. Finally, as also shown in FIGS. 57-58, the bone plate 320 may be secured to the bones 342, 344, 346, 348 with bone fasteners or bone screws 352 inserted to avoid contacting the threaded member 240 when inserted. The bone fasteners, bone screws, or fixation devices 352 may be, for example, locking or non-locking fasteners. Although not shown, it is also contemplated that the bone plate 320 may be coupled to the bones 342, 344, 346, 348 before the threaded member 240 is inserted into the bones 342, 344, 346, 348.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-58 of the present application and the components and features of FIGS. 1-31 of International Publication No. WO 2018/157170, hereby incorporated by reference in its entirety, may be used interchangeably and in alternative combinations as would be modified or altered by one of skill in the art. Further, the steps of the surgical methods associated with FIGS. 1-58 of the present application and the surgical methods associated with FIGS. 1-31 of International Publication No. WO 2018/157170 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiment, the invention is now claimed to be:

1. A targeting guide assembly, comprising:
a guide arm, wherein the guide arm comprises:
  a body extending between a first end and a second end of the guide arm, wherein the second end comprises:
    a housing element positioned at an end of an angled portion opposite the body, wherein the housing element comprises:
      a top opening;
      a bottom opening;
      an inner cavity formed by the top opening engaging the bottom opening; and
      a channel extending into the inner cavity from an exterior surface of the housing element;
    a first protrusion extending away from the housing element on a first side; and
    a second protrusion extending away from the housing element on a second side;
  the angled portion extending in a downward direction from the body to the second end; and
  a wider portion at the first end, wherein the wider portion extends from the body in a perpendicular direction;
a guide tube coupled to the guide arm; and
a guide pin that is movably engaged to an end of the guide arm, wherein the inner cavity of the housing element of the guide arm has a sphere shape to receive a corresponding sphere of the guide pin.

2. The targeting guide assembly of claim 1, wherein the wider portion comprises:
a through hole extending along a longitudinal axis of the guide arm, wherein the through hole receives the guide tube.

3. The targeting guide assembly of claim 1, further comprising:
a drill guide for insertion into a through hole of the guide tube, wherein the drill guide comprises:
  a cylindrical portion; and
  a knob positioned at an end of the cylindrical portion; and wherein the through hole extends through the cylindrical portion and the knob along a longitudinal axis of the drill guide;
a protector member for insertion through a through hole of the drill guide, wherein the protector member comprises:
  a cylindrical portion; and
  a knob positioned at an end of the cylindrical portion; and
  wherein the through hole extends through the cylindrical portion and the knob along a longitudinal axis of the protector member;
a target pin with a first end and a second end, and wherein the target pin is received within a through hole of the protector member; and
a threaded member for insertion through the through hole of the guide tube, wherein the threaded member comprises:
  a head portion positioned at a first end of the threaded member;
  at least one cutting flute positioned at a second end of the threaded member;
  a cannulated opening extending through the threaded member along a longitudinal axis; and
  a thread positioned along at least a portion of an exterior surface of the threaded member.

4. The targeting guide assembly of claim 3, wherein the guide pin comprises:
a shaft with a first end and a second end;
a spherical member coupled to the shaft between the first end and the second end, wherein the spherical member is inserted into the inner cavity of the housing element;
a tip positioned at the second end of the shaft; and
a cylindrical protrusion positioned adjacent to the spherical member and between the spherical member and the tip.

5. The targeting guide assembly of claim 1, wherein the first protrusion comprises:
a first through hole extending through the first protrusion from a top to a bottom of the housing element;
wherein the second protrusion comprises:
a second through hole extending through the second protrusion from the top to the bottom of the housing element;
further comprising:
a first anchoring wire received within the first through hole; and
a second anchoring wire received within the second through hole.

6. The targeting guide assembly of claim 1, wherein the guide tube comprises:
a threaded portion;
a body coupled to a first end of the threaded portion and extending away from the threaded portion;
a head coupled to a second end of the threaded portion; and
a through hole extending through the head, the threaded portion, and the body along a longitudinal axis of the guide tube.

7. The targeting guide assembly of claim 6, wherein the head has a first diameter and the threaded portion has a second diameter, wherein the first diameter is larger than the second diameter, wherein the head comprises:
at least one cutout positioned circumferentially around an exterior surface of the head; and
a recessed opening extending into the head and surrounding the through hole.

8. The targeting guide assembly of claim 1, further comprising:

a holder, wherein the holder is slidably coupled to a body of the guide arm, wherein the holder comprises:

a housing with a top surface and a bottom surface;

a knob rotatably coupled to the housing;

a locking member extending through an opening in the housing; an attachment arm extending away from the bottom surface of the housing and toward the top surface of the housing parallel to the housing; and a channel formed between the housing and the attachment arm.

9. The targeting guide assembly of claim 8, wherein the housing and the attachment arm form a U-shaped structure.

10. The targeting guide assembly of claim 8, wherein the attachment arm comprises:

at least one opening extending from an exterior surface through the attachment arm to the channel.

11. The targeting guide assembly of claim 10, wherein an engagement protrusion of the knob is inserted into the at least one opening of the attachment arm to couple the holder to the body of the guide arm.

12. The targeting guide assembly of claim 11, wherein the housing further comprises:

an alignment post extending away from the bottom surface of the housing adjacent to the opening in the housing for receiving the locking member.

13. The targeting guide assembly of claim 12, wherein the locking member comprises:

a shaft, wherein the shaft engages the opening of the housing;

a knob positioned at a first end of the shaft; and an engagement portion positioned at a second end of the shaft for coupling with a bone plate.

14. The targeting guide assembly of claim 13, wherein the bone plate comprises:

a bone engaging surface opposite an exterior surface;

an engagement opening for receiving the engagement portion of the locking member of the holder to couple the targeting guide assembly to the bone plate; and a plurality of openings extending from the exterior surface to the bone engaging surface, and wherein the plurality of openings receive a plurality of bone fasteners.

15. A targeting guide assembly, comprising:

a guide arm;

a guide tube coupled to the guide arm, wherein the guide tube comprises:

a threaded portion;

a body coupled to a first end of the threaded portion and extending away from the threaded portion;

a head coupled to a second end of the threaded portion; and a through hole extending through the head, the threaded portion, and the body along a longitudinal axis of the guide tube;

wherein the head has a first diameter and the threaded portion has a second diameter, wherein the first diameter is larger than the second diameter;

wherein the head comprises:

at least one cutout positioned circumferentially around an exterior surface of the head; and a recessed opening extending into the head and surrounding the through hole;

a guide pin that is movably engaged to an end of the guide arm;

a tool with an engagement tab for engaging the at least one cutout of the head;

a drill guide for insertion into a through hole of the guide tube;

a protector member for insertion through a hole of the drill guide;

a target pin with a first end and a second end, and wherein the target pin is received within a through hole of the protector member; and a threaded member for insertion through the through hole of the guide tube, wherein a head of the drill guide engages the recessed opening of the head of the guide tube.

16. The targeting guide assembly of claim 15, further comprising:

a compression cap, comprising:

a base portion;

a plurality of tabs extending away from a second end of the base portion;

a plurality of grooves positioned between each of the plurality of tabs;

a through hole extending through the base portion and the plurality of tabs;

a plurality of teeth, wherein each of the plurality of tabs includes a tooth extending away from an interior surface of each tab and into the through hole; and a slot extending through the compression cap from a top surface to a bottom surface and from an exterior surface into the through hole;

wherein the plurality of teeth of the plurality of tabs engage a lip positioned on a proximal end of the guide tube.

17. A surgical method, comprising:

inserting a guide pin into a first bone;

securing an implant holder to a bone plate;

positioning the bone plate on the first bone and at least one second bone;

securing a guide arm to the guide pin at a second end of the guide arm;

securing an intermediate portion of the guide arm within a channel of the implant holder;

inserting a reduction guide tube into a first end of the guide arm;

inserting a drill guide into a through hole of the reduction guide tube;

inserting a protector member into a through hole of the drill guide;

inserting a target pin through the protector member and into at least one bone;

inserting two anchoring wires through two protrusions positioned on a housing element at the second end of the guide arm;

removing guide pin from the guide arm;

inserting the target pin into the at least one bone, wherein the at least one bone comprises the first bone and at least one second bone, and wherein the target pin is inserted entirely through the at least one second bone and into the first bone;

removing the protector member from the drill guide;

coupling a compression cap to a proximal end of the reduction guide tube before rotating the reduction guide tube;

rotating the reduction guide tube to perform joint reduction;

drilling a hole over the target pin;

threading an implant through the drill guide and into the at least one second bone and the first bone to secure the first bone and the at least one second bone; and inserting bone fasteners through the bone plate and into the first bone and the at least one second bone, wherein the bone fasteners are inserted into the first bone and the at least one second bone to avoid contacting the implant, wherein the implant is inserted before the bone fasteners, and wherein the implant is inserted after the bone fasteners and avoids contacting the bone fasteners.

\* \* \* \* \*